US009623125B2

(12) United States Patent
Vicent Docon et al.

(10) Patent No.: US 9,623,125 B2
(45) Date of Patent: Apr. 18, 2017

(54) CONTROLLED SYNTHESIS OF POLYGLUTAMATES WITH LOW POLYDISPERSITY AND VERSATILE ARCHITECTURES

(71) Applicant: Fundacion de la Comunidad Valenciana "Centro De Investigaciones Principe Felipe", Valencia (ES)

(72) Inventors: Maria Jesus Vicent Docon, Valencia (ES); Matthias Barz, Valencia (ES); Fabiana Canal, Valencia (ES); Inmaculada Conejos Sanchez, Valencia (ES); Aroa Duro Castano, Valencia (ES); Richard Mark England, Valencia (ES)

(73) Assignee: Fundacion de la Comunidad Valenciana "Centro de Investigaciones Principe Felipe", Valencia (ES)

( * ) Notice: Subject to any disclaimer, the term of this patent is extended or adjusted under 35 U.S.C. 154(b) by 0 days.

(21) Appl. No.: 14/351,904

(22) PCT Filed: Oct. 23, 2012

(86) PCT No.: PCT/ES2012/070740
§ 371 (c)(1),
(2) Date: Apr. 15, 2014

(87) PCT Pub. No.: WO2013/060919
PCT Pub. Date: May 2, 2013

(65) Prior Publication Data
US 2015/0087788 A1 Mar. 26, 2015

(30) Foreign Application Priority Data
Oct. 24, 2011 (ES) .................................. 201131713

(51) Int. Cl.
| | |
|---|---|
| *A61K 49/14* | (2006.01) |
| *A61K 47/48* | (2006.01) |
| *C08G 69/48* | (2006.01) |
| *C08G 69/08* | (2006.01) |
| *C08G 69/10* | (2006.01) |
| *A61K 51/08* | (2006.01) |
| *C07K 2/00* | (2006.01) |

(52) U.S. Cl.
CPC ...... *A61K 49/146* (2013.01); *A61K 47/48215* (2013.01); *A61K 47/48315* (2013.01); *A61K 51/08* (2013.01); *C08G 69/08* (2013.01); *C08G 69/10* (2013.01); *C08G 69/48* (2013.01); *C07K 2/00* (2013.01)

(58) Field of Classification Search
CPC ........ A61K 47/48215; A61K 47/48315; A61K 49/146; A61K 51/08; C08G 69/08; C08G 69/10; C08G 69/48; C07K 2/00

USPC .................................. 528/298, 292; 525/410
See application file for complete search history.

(56) References Cited

U.S. PATENT DOCUMENTS

| | | | |
|---|---|---|---|
| 2008/0279778 A1* | 11/2008 | Van et al. ...................... 424/9.3 |
| 2011/0207686 A1* | 8/2011 | Lecommandoux .. A61K 9/0019 514/34 |

OTHER PUBLICATIONS

Thambi et al. ("Bioreducible Block Copolymers Based on Poly(Ethylene Glycol) and Poly(γ-Benzyl L-Glutamate) for Intracellular Delivery of Camptothecin", Bioconjugate Chem., 2011, 22 (10), pp. 1924-1931, Publication Date (Web): Sep. 7, 2011).*

(Continued)

*Primary Examiner* — Ling Choi
*Assistant Examiner* — Chun-Cheng Wang
(74) *Attorney, Agent, or Firm* — Hayes Soloway PC

(57) ABSTRACT

Polyglutamates are well known to be highly biocompatible, biodegradable and multifunctional polymers, which have been already used as building blocks in polymer drug conjugates and polymeric micelles. Those systems have been applied to various medical applications ranging from therapy to molecular imaging. Furthermore a polyglutamic acid (PGA) paclitaxel conjugate has already entered clinical studies (Opaxio™ PGA-PTX conjugate currently in phase III of Clinical trials).

Figure 1:
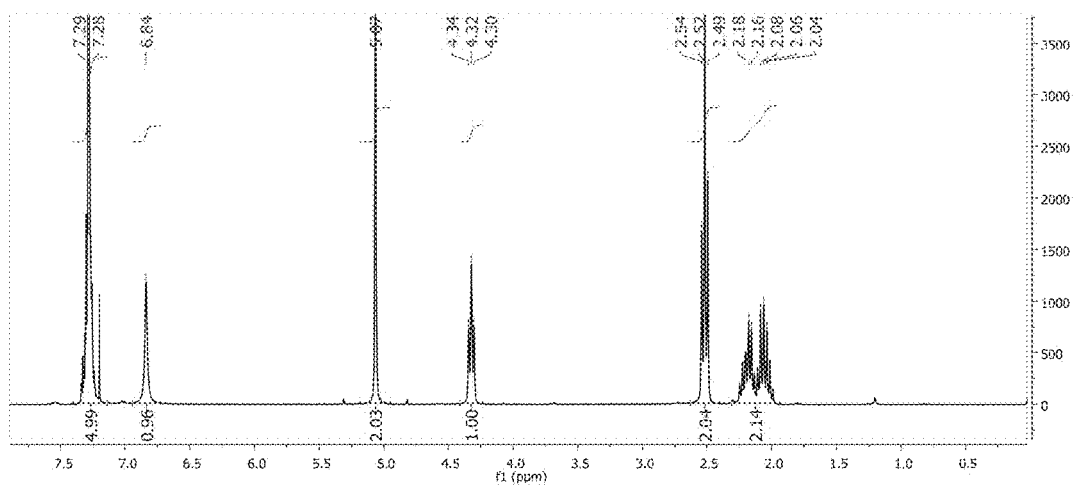

In this context, a synthetic pathway to a plethora functional polyglutamates (homopolymers, block-co-polymers, tri-bocks) with well-defined structure, adjustable molecular weight (Mw) and low dispersity (Đ=Mw/Mn<1.2) applying the ring opening polymerization (ROP) of N-carboxyanhydrides (NCA) has been developed. Additionally, the acid moieties of the polyglutamates can be activated with 4-(4, 6-dimethoxy-1,3,5-triazin-2-yl)-4-methylmorpholinium (DMTMM) and various functionalities can be easily introduced by "post-polymerization modification" yielding a set orthogonal reactive attachment sides. The reactive moieties, such as azides, maleimides, thiols, akynes (linear or cyclic) offer the opportunity of specific conjugation of the drugs, targeting moieties or markers. Besides introducing reactive groups the functionalization strategy was also used for PEGylation of PGA reducing charge induced interactions and therefore pharmacological properties, such as blood circulation time may be adjusted.

In summary, a tool kit of various polyglutamates has been developed enabling the synthesis of a variety of polymer drug conjugates or polymer based imaging agents. The functional polymeric precursors developed will allow us to functionalize and therefore adjust the polymer properties to a desired application.

23 Claims, 12 Drawing Sheets

(56) References Cited

OTHER PUBLICATIONS

Mori et al, ("Ring-Opening Polymerization of y-benzyl-L-glutamate-N-carboxyanhydride in ionic liquids", Elservier, Ltd., Polymer 49 (2007) 5867-5877).*
Chun Li ("Poly(L-glutamic acid)-anticancer drug conjugates", Advanced Drug Delivery Reviews 54 (2002) 695-713).*
Melancon et al. ("Multifunctional Synthetic Poly(L-Glutamic Acid)-Based Cancer Therapeutic and Imaging Agents", Molecular Imaging, vol. 10, No. 1 (Jan.-Feb. 2011): pp. 28-42).*
Guo-Quan Zhu ("Properties of a poly(ethylene glycol)-block-poly(γ-benzyl L-glutamate)-graft-poly(ethylene glycol) copolymer membrane", Chemical Papers 64 (1) 34-39 (2010), First Online: Oct. 22, 2009).*
Jeong et al. ("Adriamycin release from flower-type polymeric micelle based on star-block copolymer composed of poly(γ-benzyl l-glutamate) as the hydrophobic part and poly(ethylene oxide) as the hydrophilic part", International Journal of Pharmaceutics, vol. 188, Issue 1, Oct. 15, 1999, pp. 49-58).*
Wang et al. ("Synthesis and Characterization of Poly(L-Glutamic Acid-co-L-Aspartic Acid)", Chinese Journal of Polymer Science vol. 26, No. 4, (2008), 381-391).*
Mori et al, "Ring-Opening Polymerization of y-benzyl-L-glutamate-N-carboxyanhydride in ionic liquids", Elservier, Ltd., Polymer 49 (2007) 5867-5877.
Dimitrov et al, "Synthesis of nearly monodisperse polystryene-polypeptide block copolymers via polymerisation of N-carboxyanhydrides", The Royal Society of Chemistry, Chem Commun, 2003, 2944-2945.
Kamei et al, "Synthesis of Polypeptide-Polyether conjugates from an Activated Urethane Derivative of y-Benzyl-L-glutamate as a Monomer", Polymer Bulletin 60, (2008) 625-633.
Deming, "Polypeptide and Polypeptide Hybrid Copolymer Synthesis via NCA Polymerization", Adv. Polym Sci (2006) 202: 1-18.
Gaspar et al, "Polymeric carriers: Preclinical safety and the regulatory implications for design and development of polymer therapeutics", Elservier, Advanced Drug Delivery Reviews 61, (2009) 1220-1231.
Barz et al, "Overcoming the PEG-addiction: well-defined alternatives to PEG, from structure-property relationships to better defined therapeutics", The Royal Society of Chemistry, Polym. Chem, 2011, 2, 1990.
Wang et al, "Fibrous proteins and tissue engineering", Materials Today, Dec. 2006, vol. 9, No. 12.
Li et al, "Polymer-drug Conjugates" Recent development in Clinical Oncology, NIH Public Access, Adv. Drug Deliv Rev. May 22, 2008 (60)8: 886-898.
Darcy et al, "Translational Research in the Gynecologic Oncology Group: Evaluation of Ovarian Cancer Markers, Profiles and Novel Therapies", NIH Public Access, Gynecol Oncol. Jun. 2010; 117(3), 429-439.
Aliferis et al, "Rapid Communication: Well-defined linear multiblock and branched polypeptides by Linking Chemistry", Journal of Polymer Science: Part A, Polymer Chemistry, col. 43, 4670-4673 (2005).
Knobler et al, "Reaction of N-carboxy-α-amino-acid anhydrides with hydrochlorides of hydroxylamine, O-alkylhydroxylamines, and amines; syntheses of amino-hydroxamic acids, amido-oxy-peptides, and α-amino-acid amides", J. Chem So. 1964, 3941-3951.
Knobler et al, "a-Aminoacyl Derivatives of Aminobenzoic Acid and of Amino-oxy-acids by Reaction of their Hydrochlorides with Amino-acid N-Carboxy-anhydrides", J. Chem So. 1969, 1821-1824.

* cited by examiner

A                                    B (A)

(B)

CONTROLLED SYNTHESIS OF POLYGLUTAMATES WITH LOW POLYDISPERSITY AND VERSATILE ARCHITECTURES

The present invention relates to controlling the polymerization of O-Amino Acid N-Carboxyanhydrides (NCAs) by the use of non-nucleophilic salts to obtain low polydispersed polypeptides (as homopolymer, diblock, triblock or multiblock systems) of highly versatile architectures, as well as to processes for their preparation, to pharmaceutical compositions containing them and their use in medicine.

BACKGROUND ART

An ideal polymer to be used as carrier for drug delivery or molecular imaging should be characterized by (i) biodegradability or adequate molecular weight that allows elimination from the body to avoid progressive accumulation in vivo; (ii) low polydispersity, to ensure an acceptable homogeneity of the final system allowing to adjust pharmacokinetics; (iii) longer body residence time either to prolong the conjugate action or to allow distribution and accumulation in the desired body compartments (therefore high molecular weights are desired); and (iv) for protein conjugation, only one reactive group to avoid crosslinking (semitelechelic polymers), whereas for small drug conjugation, many reactive groups to achieve a satisfactory drug loading (multivalent polymers).

Because of their implicit nature, polymers present specific challenges for the pharmaceutical development. A manufactured drug substance should be homogeneous and composed of single, defined specie. By contrast, all synthetic polymers are inherently heterogeneous and, as macromolecules, they can bear special challenges for characterization. The total control of crucial parameters such as molecular weight, polydispersity, localization of charge or hydrophobicity-hydrophilicity balance is a must in order to tune body biodistribution, fate, biological activity and toxicity [1,2]. The average molecular weight is described by the "weight average molecular weight" (Mw) and "number average molecular weight" (Mn) and the ratio Mw/Mn gives a measure of the dispersity D.

Therefore there is an interest in finding methodologies to enhance polymer molecular weight for biodegradable systems controlling the homogeneity in the process and allowing a high degree of versatile to be implemented in different clinical needs.

The ring-opening polymerization (ROP) of amino acid-N-carboxyanhydrides (NCA) is the most commonly applied polymerization technique to produce polypeptides and polypeptide-based block copolymers on a several gram scale. Although the obtained polymers are less defined than peptides produced by a natural organism the polymerization method enables access to polypeptidic architectures, which are beyond nature's possibilities. Furthermore the ROP of NCAs has already been applied to various applications in different fields of science. Those applications range from drug delivery systems or molecular imaging systems to surface coating materials [2-6].

As a prominent example for the use of the NCA polymerization one has to mention a conjugate of polyglutamic acid (PGA) and paclitaxel (Opaxio®, formerly Xyotax, PPX, CT-2103). The polymer drug conjugate has entered clinical phase 3 trails 7-[9] emphasizing the importance of the NCA polymerization method for the preparation of well-defined synthetic polypeptides. Polyglutamic acid is promising material for the design of nanomedicines due to its high biocompatibility, multivalency and in vivo degradability by thiol proteases (cathepsin B). [10-11]

From the historic point of view the NCA polymerization is a rather old method. It was discovered by Leuch in the beginning of the 20th century. [12-14] In respect to this fact various methods have been reported for the ROP of NCAs as reviewed in following excellent literature. [15-17] So far the most promising chemical approaches are based on initiation of purified NCAs with primary amines and high vacuum techniques, [18-20] use of amine hydrochloride salts as initiators [21], heavy metal catalysts [22-24] or hexamethyldisilazanes (HMDS) [25-26]

Unfortunately, most of those methods have certain limitations in the synthesis of well-defined polypeptides. Hexamethyldisilazanes (HMDS) amines are sensitive to hydrolytic reactions. While heavy metal catalysts have to be removed afterwards whenever biomedical applications are desired. The removal is both time consuming and incomplete.

The normal initiation with a primary amine (NA) leads in most cases to reduced control about the polymerization process itself. Especially whenever a higher degree of polymerization or complex architectures are desired the occurring side reactions interfere. In general Polyglutamates with a molecular weight average ranging from some thousands up to 50 kg/mol and PDIs of 1.2 to 1.5 are reported in literature [17]. Large PDI values are in all probability to be attributed to the fact that NCA polymerization suffers from side reactions. The most likely one is the "activated monomer" process (AM), initiated by the deprotonaton of an NCA molecule. The NCA anion is a sufficiently strong nucleophile to initiate the oligomerization of NCAs. The formed N-aminoacyl NCA compounds will either add to the propagating chain end or undergo self-condensation, the latter reaction producing high molecular weight products at high monomer conversion. Since primary amines can act as both a nucleophile and a base, polymerization will always switch back and forth between the "amine" and the "activated monomer" mechanism (NAM).

By lowering the reaction temperature the polypeptides may get more defined, because side reactions are suppressed, but reaction times increase about 2-4 times while yield decreases [27-29]. However, for the production of block copolymers (diblock, triblock or multiblock), NCA polymerization should preferably proceed until high conversions via the "amine" mechanism, i.e. nudeophilic ring-opening of the NCA leading to defined end groups. The control over polymer end groups is essential for the synthesis of multiblock architectures. [30]

The "activated monomer" pathway might be avoided simply by adding an acid, inducing the re-protonation of eventually formed NCA anions. Nevertheless this idea is not new. Basically, this idea goes back to the work of Knobler et al. published in the 1960s [31-32]. These authors investigated the stoichiometric reaction between NCAs and the hydrochlorides of primary amines for the preparation of aminoacyl compounds. Schlaad and coworkers have used this method to prepare well-defined Polystyrene based block copolymers. [21]

The disadvantage of this approach is the fact that the chloride ion itself can act either as a nucleophile or base deprotonating the NCA and therefore side reactions e.g., initiation of the NCA ring opening by the activated monomer mechanism (AMM) as already demonstrated by Schlaad [21] and was reproduced in our lab (for analytical data of the HCl induced polymerization of glutamic acid based NCAs is included for comparison (see Table 1)).

TABLE 1

Comparison between Normal Amine and Schlaad NCA polymerization approaches.

| Initiator | P | [M]/[I] | DP Calc. a) | DP ¹H-NMR | [M] Mol | t reaction (d) | Yield | Mn | Mw | PDI |
|---|---|---|---|---|---|---|---|---|---|---|
| NAM 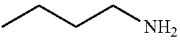 | 1 | 100 | 77 | 41 | 0.38 | 3 | 77 | 20.3 | 25.4 | 1.2 |
| | 2 | 400 | 300 | 59 | 0.38 | 3 | 75 | 22.4 | 31.9 | 1.4 |
| | 3 | 160 | 1328 | 60 | 0.38 | 3 | 83 | 20.5 | 28.3 | 1.4 |
| Schlaad 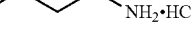 | 4 | 100 | 60 | 36 | 0.38 | 3 | 60 | 4.4 | 5.6 | 1.3 |
| | 5 | 400 | 288 | 55 | 0.38 | 3 | 72 | 18.1 | 27.2 | 1.5 |
| | 6 | 1600 | 1168 | 90 | 0.38 | 3 | 73 | 20.7 | 31.2 | 1.5 |

P: Polymer,
[M]/[I]: Monomer to Initiator ratio;
DP: Degree of polymerization (% of [M]/[I];)
Mw: weight average molecular weight;
Mn: number average molecular weight
PDI: polydispersity index (ratio Mw/Mn that gives a measure of the dispersity D).

$^{a)}$Calculated using $DP = \frac{[M]}{[I]} \cdot con$

As shown in Table 1, although both methods are easy to apply without complicated equipment or complex synthesis they are invalid whenever a degree of polymerization (DP) above 100 is desired. Thus, there is a need for a different approach.

SUMMARY OF THE INVENTION

The present invention was made in view of the prior art described above, and the object of the present invention is to enhance degree of polymerization (DP), structural versatility and decrease polydispersity index (PDI) of polypeptides obtained by polymerization of N-carboxyanhydrides of alpha-amino acids (NCA).

To solve the problem, the present invention provides the substitution of the chloride by a non-nucleophilic anion, such as tetrafluoroborone. Thus, side reactions based on the nucleophilic character of the counter ion have been effectively suppressed. Therefore the control over polymer end groups has been enhanced enabling the synthesis of well-defined homo, diblock or triblock polypeptides of a variety of molecular weight and side-chain and terminal chain functionalities.

FIGURE DESCRIPTION

FIG. 1: ¹H-NMR spectra of the y-Benzyl L-Glutamate N-Carboxyanhydride (NCA)

Figure 2:
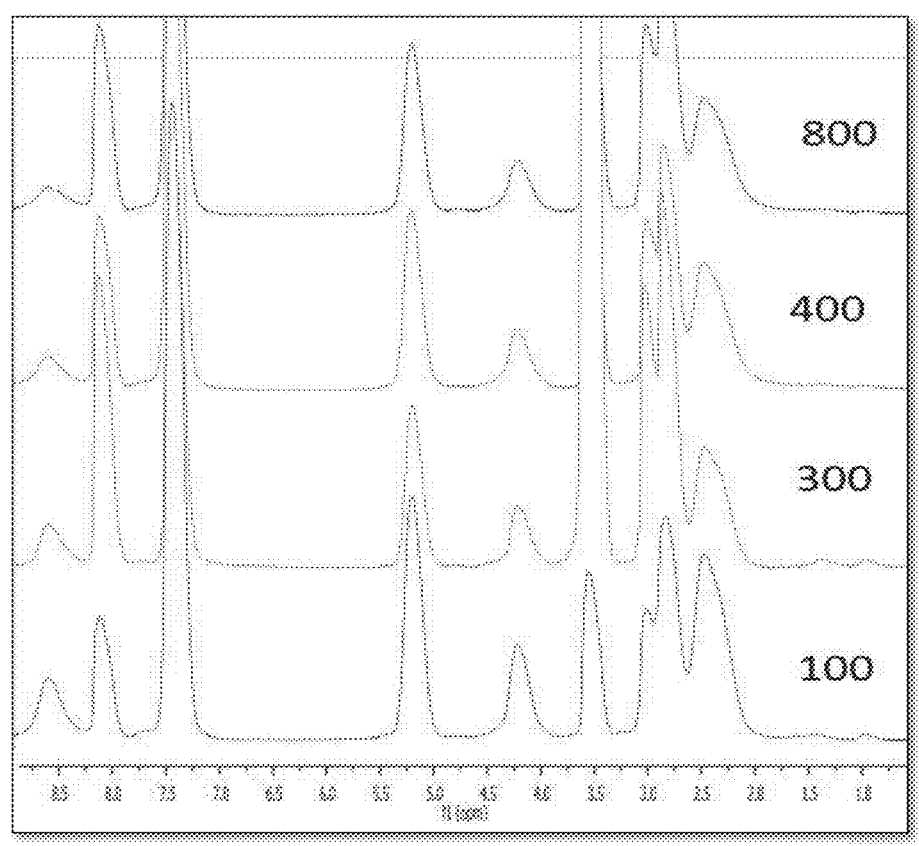
Figure 3:
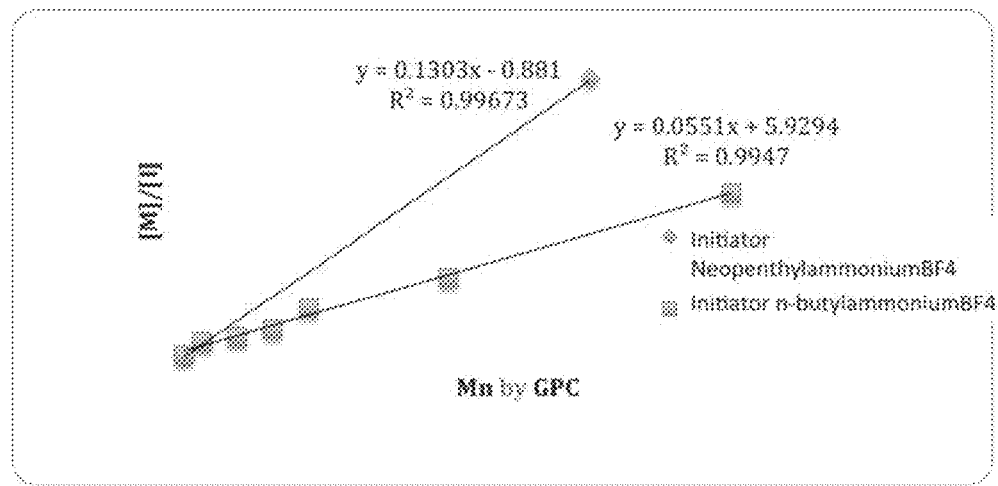
Figure 4:
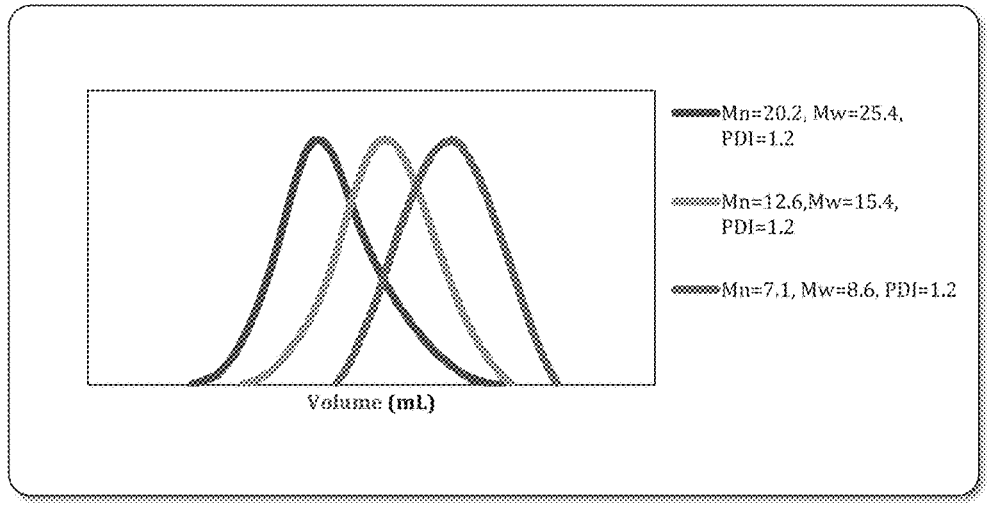
Figure 6:
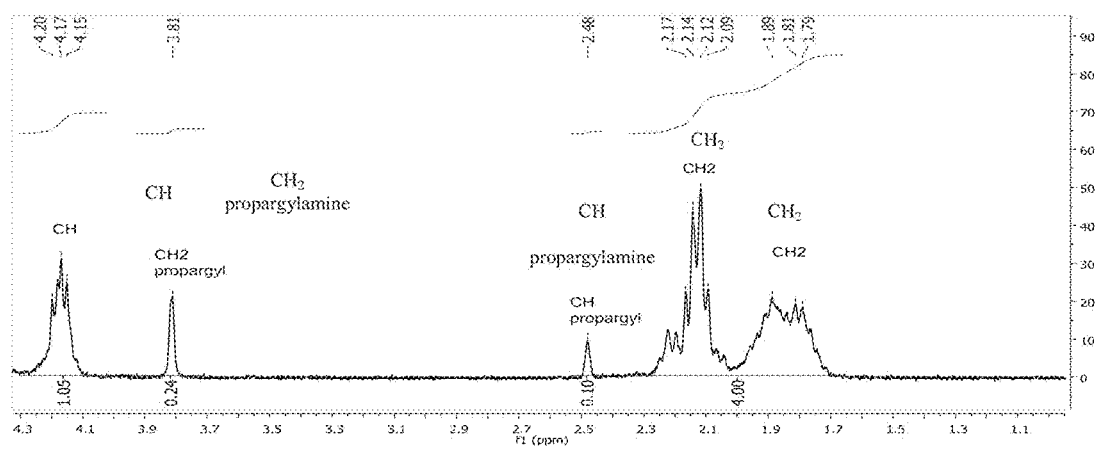
Figure 7:
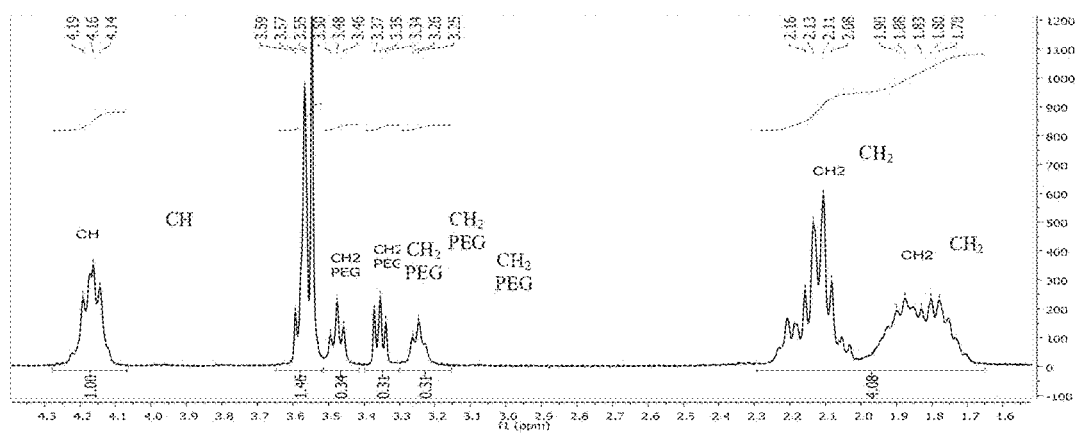

FIG. 2: ¹H-NMR spectra of polymerizations carried out with n-butyl tetrafluoroboran salts at different [M]/[I] ratio of polymerization in DMF FIG. 3: Representation of [M]/[I] ratio versus Mn by GPC FIG. 4: GPC elugrams of several polyglutamates with different molecular FIG. 5: ¹H-NMR spectra of deprotected n-butil-α-poliglutamic acid corresponding to the batch that was scaled up to 5 grams. DP=252 as confirmed by NMR, FIG. 6: ¹H-NMR spectra of a PGA derivative modified with propagylamine FIG. 7: ¹H-NMR spectra of a PGA derivative modified with oligoEG-azide groups.

Figure 8:
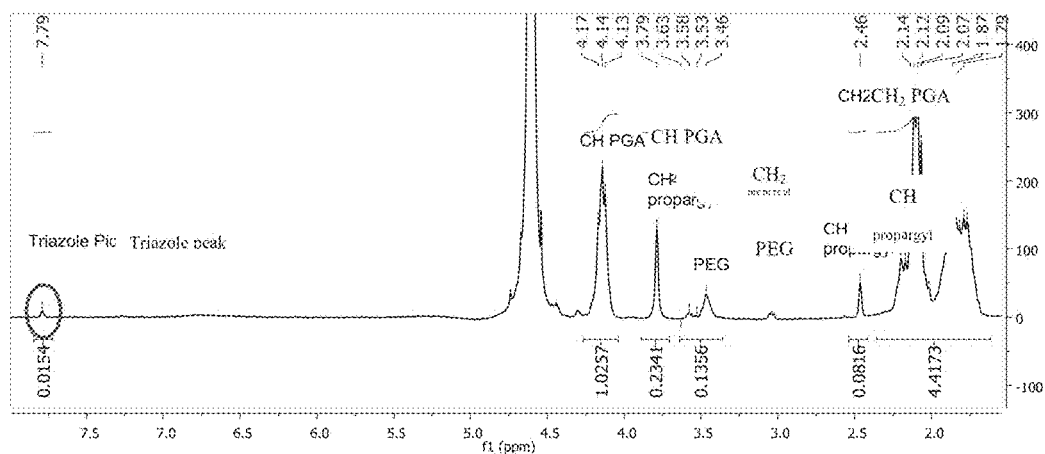

FIG. 8: ¹H-NMR spectra of the copolymer resulting from the linking of PGA-propargylamine with $NH_2PEG(2)N_3$.

Figure 9:
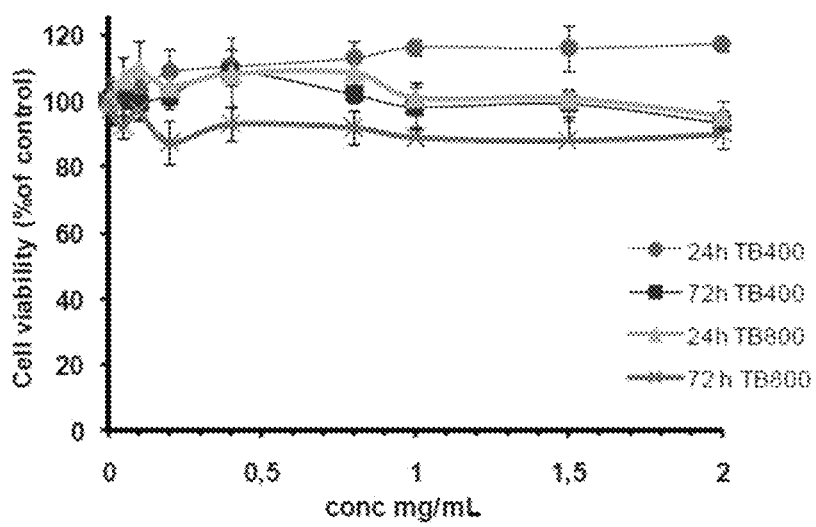
Figure 9:
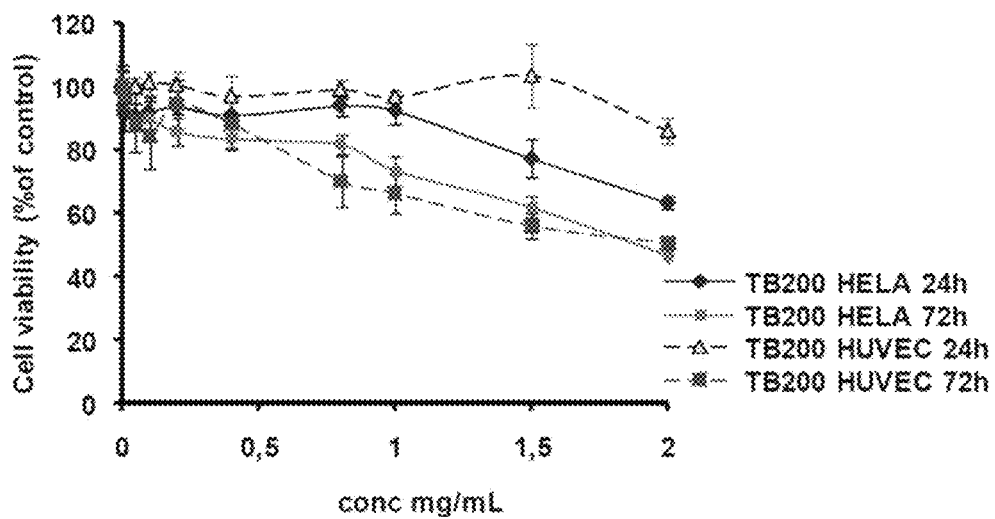

FIG. 9A: MTT evaluation of cell viability of TB400 [P: 35 wherein X=OMe or S-S-4TP] and TB800 [P: 36 wherein X=OMe or S-S-4TP] in HUVEC cells at different incubation times.

FIG. 9B: MTT evaluation of cell viability of TB200 [P: 34 wherein X=OMe or S-S-4TP in HUVEC and HeLa cells at different incubation times.

Figure 10:
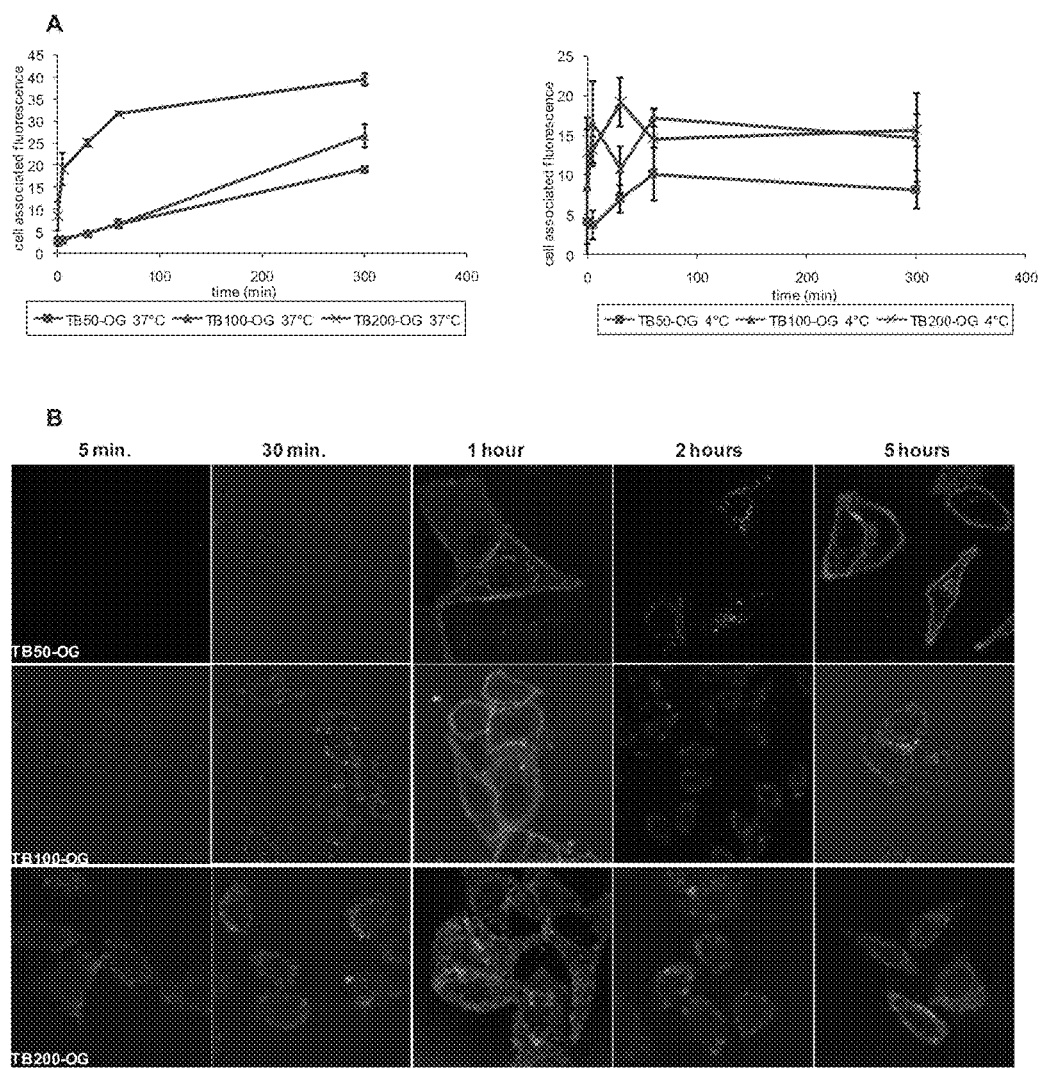

FIG. 10A: Cellular internalization kinetics with triblocks synthesized and labelled with oregon green (TB-OG50 [P: 41 wherein $R_1$=MeO-PEG2000, $R_2$=—NH-PEG2000-OMe, $R_3$=ONa], TB-OG100 [P: 42 wherein $R_1$=MeO-PEG2000, $R_2$=—NH-PEG2000-OMe, $R_3$=ONa], and TB-OG200[P: 43 wherein $R_1$=MeO-PEG2000, $R_2$=—NH-PEG2000-OMe, $R_3$=ONa]). Flow cytometry assays at 37° C. and 4° C. (inhibition of energy-dependent cellular internalization mechanism like endocytosis).

FIG. 10B: Cellular internalization kinetics with triblocks synthesized and labelled with oregon green (TB-OG50 [P: 41 wherein $R_1$=MeO-PEG2000, $R_2$=—NH-PEG2000-OMe, $R_3$=ONa], TB-OG100 [P: 42 wherein $R_1$=MeO-PEG2000, $R_2$=—NH-PEG2000-OMe, $R_3$=ONa], and TB-OG200[P: 43 wherein $R_1$=MeO-PEG2000, $R_2$=—NH-PEG2000-OMe, $R_3$=ONa]). Live-cell confocal microscopy of HeLa cells at different incubation times (5 min, 30 min, 1 h, 2 h y 5 h). Images correspond to TB-OG (green) internalization in the presence of a lipid membrane marker (red) at 1 h and 5 h.

Figure 11:
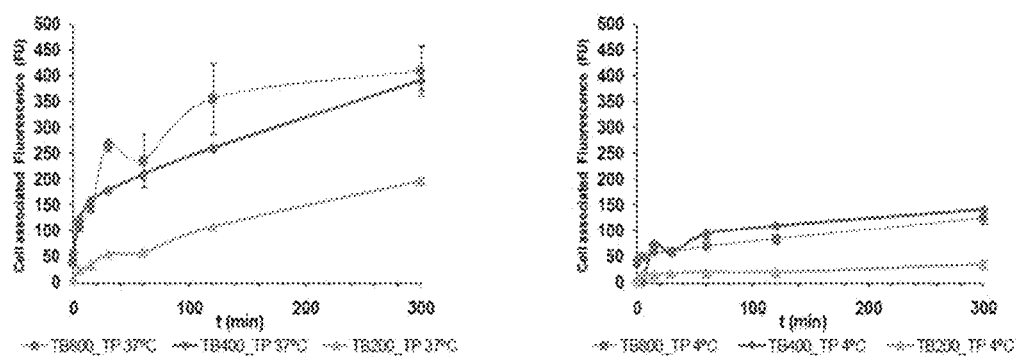
Figure 11:
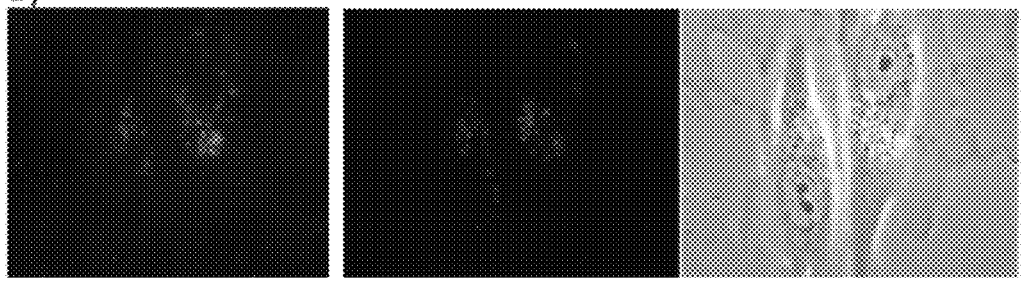

FIG. 11A: Cellular internalization kinetics with triblocks synthesized and labelled with oregon green. Flow cytometry assays at 37° C. and 4° C. (inhibition of energy-dependent cellular internalization mechanism like endocytosis).G2000, $R_2$=—NH-PEG3000-S-S-4TP, $R_3$=ONa] and TBOG800_4TP [P: 44 wherein R₁=MeO-PEG2000, R₂=—NH-PEG3000-S-S-4TP, R₃=ONa]).

FIG. 11B. Cellular internalization kinetics with triblocks synthesized and labelled with oregon green. Live-cell confocal microscopy of HUVEC cells with TB-OG200_TP at 2 h of incubation. Dextran Texas Red as lysosomal marker (red).

Figure 12A:
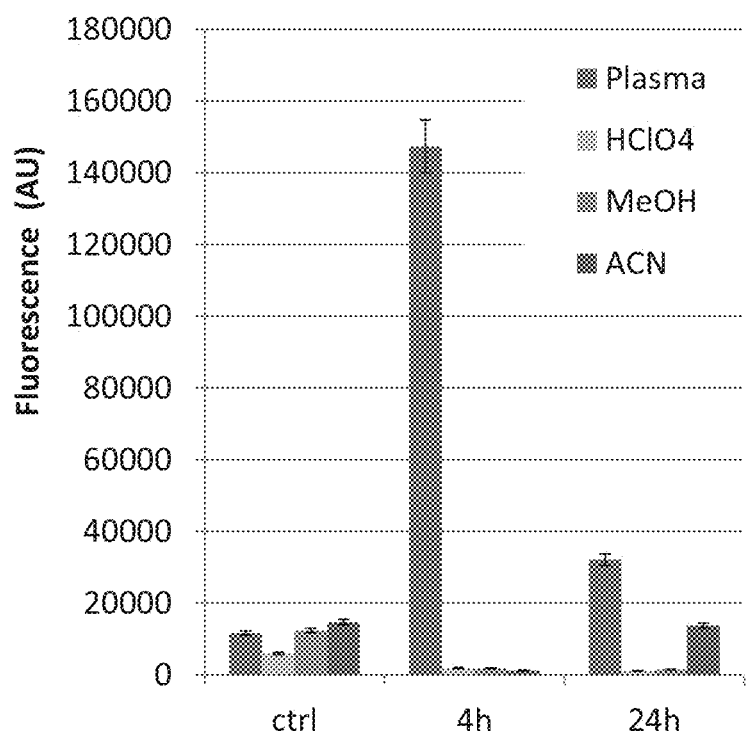

FIG. 12A: Fluorescence measure of serum with espectrofluorometer at different times after animal sacrifice and subsequent serum treatments: direct measure of serum (plasma), measure of the supernatant after homogenation with HClO₄ (HClO₄) measure after washing the pellet with methanol (MeOH) and measure after washing the pellet with acetonitrile(AcN)

Figure 12B:
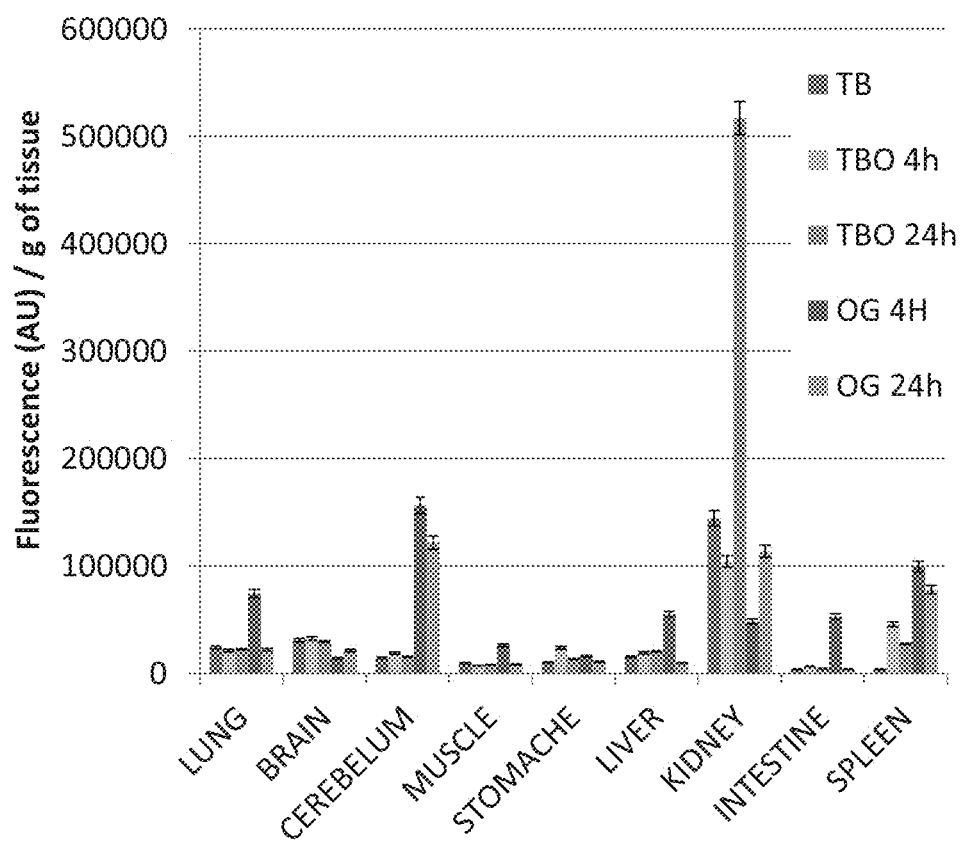

FIG. 12B. Measures of the fluorescence of the different organ homogenate (liver, kidney, intestine, spleen, brain, muscle, cerebelum and lung) after 4 and 24 h post injection. TB=TB200 [P:34 wherein X=—S-S-4TP], TBO 4=TB-OG200_4TP [P: 43 wherein R₁=MeO-PEG2000, R₂=—NH-PEG3000-S-S-4TP, Rs=ONa], (4 h), TBO 24=TB-OG200_4TP [P: 43 wherein R₁=MeO-PEG2000, R₂=—NH-PEG3000-S-S-4TP, R₃=ONa], (24 h).

Figure 13:
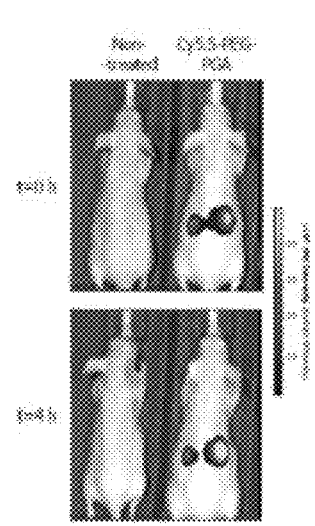
Figure 13:
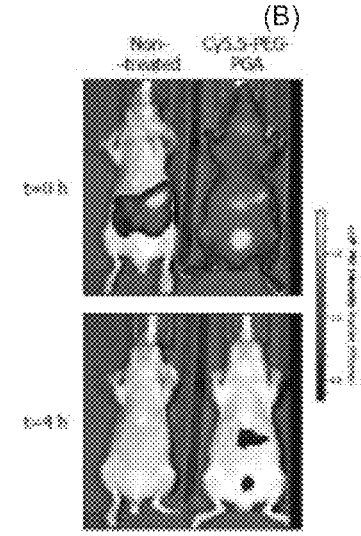

FIG. 13. IVIS®Spectrum image. DB100-Cy5.5 4 h monitoring after injection. Renal elimination of the polymeric transporter (A) Dorsal position (B) Ventral position FIG. 14A: Magnetic resonance image of the head of the rat before injection of the compound TB800-DTPA/Gd FIG. 14B: Magnetic resonance image of the head of the rat after injection of the compound TB800-DTPA/Gd FIG. 15 PET/CT image. PGA-DOTA-⁶⁸Ga (50.5 µCi) monitorization. (A) PGA-DOTA-⁶⁸Ga structure used in this example. Sagittal section 18 min after i.v. administration, image adquisition 60 min. Renal elimination of polymeric transporter. (B) Sagittal, ventral and dorsal sections

DETAILED DESCRIPTION OF THE INVENTION

One aspect of the present invention relates to the provision of a new methodology for controlling the polymerization of O-amino acid N-carboxyanhydrides by the use of non-nucleophilic salts, such as, ammonium tetrafluoroborone salts, general method used as follows:

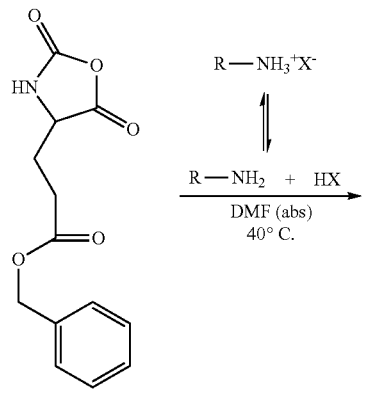

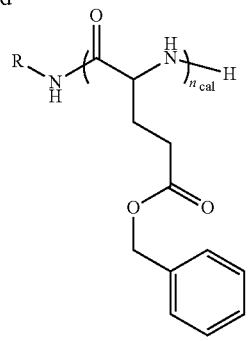

wherein
R represents alkyl, Defined C-terminal Attachment sites (Alkyne, azide, activated thiols, etc.), ethyleneglycol (EG) of different sizes including polyethylenglycol (PEG from Mw range 100 to 10000 g/mol)
n represents number of repeating units of y-benzylglutamate in the polymer ranging from 1 to 1.000 units The tetrafluoroborone ammonium salts can be easily prepared by the reaction of the corresponding amine with the HBF₄ diethylether complex, purified and stored without detected decomposition or impurities.

Another aspect of the present invention relates to different di- or tri-blocks systems with adequate end-group functionality to allow further site-specific conjugation, a polymer which is a di- or -triblock with general structures as follows:

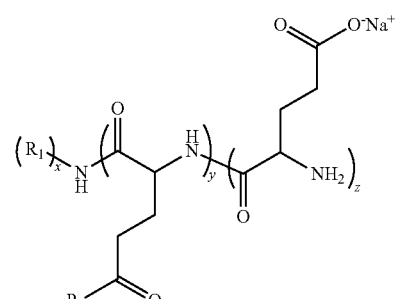

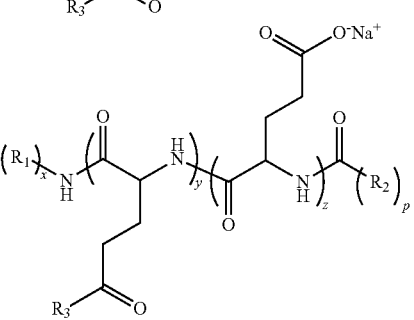

wherein:
R1 represents alkyl, Defined C-terminal attachment site (Alkyne, azide, activated thiols, halides, alkenes, activated esters, activated alcohols, protected amines, maleimide groups, acetals, activated caboxylic acids), ethyleneglycol (EG) of different sizes including polyethylenglycol (PEG from Mw range 100 to 10000 g/mol)
R2 represents alkyl, Defined C-terminal attachment sites (Alkyne, azide, activated thiols, halides, alkenes, activated esters, activated alcohols, protected amines, maleimide groups, acetals, activated caboxylic acids), ethyleneglycol (EG) of different sizes including polyethylenglycol (PEG from Mw range 100 to 10000 g/mol), PEG-thiol, PEG-4TP R3 represents alkyl, Defined C-terminal Attachment sites (Alkyne, azide, activated thiols, halides, alkenes, activated esters, activated alcohols, protected amines, maleimide groups, acetals, activated caboxylic acids), (EG) of different sizes including polyethylenglycol (PEG from n=2 to n=16), aminoacids (including Lysine, Arginine, imidazole, histidine, cysteine as well as secondary and tertiary amino groups)

x represents number of monomer units included into R1 definition from 1 to 500 y represents number glutamic units modified with R3 group in the polymer, from 1 to 500 z represents number of glutamic units without modification in the polymer, from 1 to 1000 p represents number of monomer units included into R3 definition, from 1 to 500

R2 and R3 can be used to conjugate bioactive agents (including low Mw drugs, peptides, proteins, antibodies), fluorescence/NIR probes, coordination complexes for MRI, PET and SPECT probes As used therein in this patent, the term "treatment" includes treatment, prevention and management of such condition. The term "pharmaceutically acceptable" as used herein refers to those compounds, compositions, and/or dosage forms which are, within the scope of medical judgement, suitable for use in contact with the tissues of humans and animals without excessive toxicity, irritation, allergic response, or other problem or complication, commensurate with a reasonable benefit/risk ratio.

In different particular embodiments of the invention R represents n-Butylamine, R1 represents m-PEG, R2 represents PEG optionally bearing an end-group functionality including (—OH, —SH, —S-S-4TP, any —S— protected derivate, —NH$_2$, alkyne, azide, maleimide) with one or more substituents selected from halogen. In another embodiment R3 represents -EG-alkyne, EG-azide, alkyl, optionally substituted. In another embodiment R3 represents —(CH$_2$)$_2$-phenyl optionally substituted with one or more substituents selected from halogen. In another embodiment R3 represents coordination complexes, as for example Gd-DTPA or Ga-DOTA, Tc-DTPA, Cu-polyamine.

In the polymer drug conjugate, the polyglutamic acid may be poly-L-glutamic acid, poly-D-glutamic acid or poly-DL-glutamic acid. In one embodiment of the invention polyglutamic acid is poly(L-glutamic acid).

Furthermore, all possible combinations of the above-mentioned embodiments form also part of this invention.

The present invention relates to a process for the preparation of the above said novel compounds, their derivatives, their analogues, their tautomeric forms, their stereoisomers, their polymorphs or their pharmaceutical acceptable salts and solvates.

The polymers of the present invention are carriers for delivery and administration of drugs or molecular imaging agents. Therefore, they are useful for the diagnosis, treatment or prevention of pathologies depending on the conjugated cargo.

The polymers and the conjugated derivatives of the present invention can be administered in the form of any pharmaceutical formulation. The pharmaceutical formulation will depend upon the nature of the active compound and its route of administration. Any route of administration may be used, for example such as oral, buccal, pulmonary, topical, parenteral (including subcutaneous, intramuscular, and intravenous), transdermal, ocular (ophthalmic), inhalation, intranasal, otic, transmucosal, implant or rectal administration.

Injectable preparations for parenteral administration comprise sterile solutions, suspensions or sterile emulsions in oily or aqueous vehicles, and may contain coadjuvants, such as suspending, stabilizing, tonicity agents or dispersing agents.

The compound can also be formulated for its topical application. Formulations include serums, creams, lotions, gels, powders, solutions, shampoo preparations, oral paste, mouth wash preparations and patches wherein the compound is dispersed or dissolved in suitable excipients.

In one embodiment of the invention the pharmaceutical composition is in the form of nanospheres, microparticles and nanoparticles.

Synthesis of y-Benzyl L-Glutamate N-Carboxyanhydride (NCA) from L-Glutamic Acid y-Benzyl Ester and Diphosgene by Using Limonene as HCl Cleavage α-Amino acid N-carboxy anhydrides (NCAs) synthesis can be divided into two groups depending on the nature of the amino acid substrate. The first is the Leuchs method and is based on the cyclization of N-alkoxycarbonyl amino acid halides to form the α-amino acid N-carboxy anhydride. The second is called the Fuchs-Farthing method, and involves the direct phosgenation of unprotected α-amino acids, see y-Benzyl-L-glutamate N-Carboxyanhydride synthesis below.

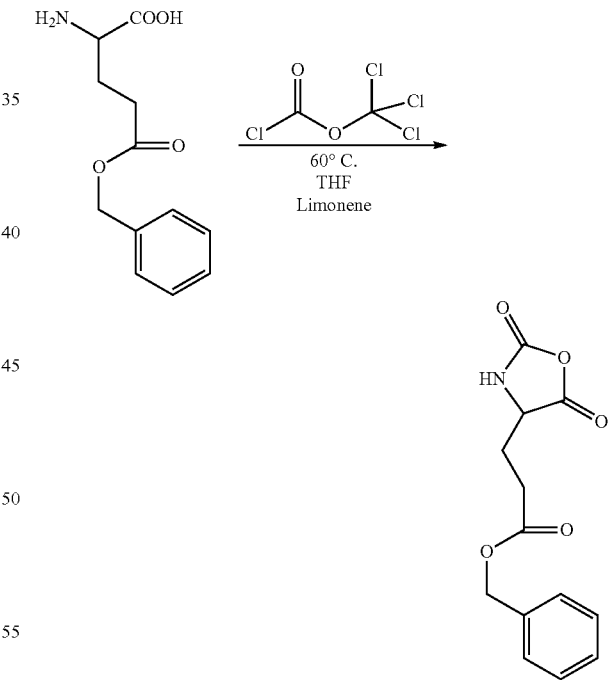

The protocol was adapted from N.M.B Smeets et al. "A Scalable synthesis of L-Leucine-N-carboxyanhydre". Organic Process Research & Development 2005, 9, 757-763 a variation of the Fuchs-Farthing method. In addition, some variations like the removal of remaining phosgene or HCl by a nitrogen flow prior to precipitation followed by recrystallization and filtration under Schlenk conditions to avoid impurities and enhance storage stability. Phosgene could have been used in the reaction, but this would lead to a lack of stoichiometric control. As a result excessive use of phosgene is likely to occur generating the formation of the contaminations. Those are the amino acid chloride hydrochloride formed by the HCl cleavage of the NCA ring, which can be phosgenated in a second step to form α-isocyanate acid chlorides. Both byproducts are critical in the polymerization of NCAs and will lead to a broad or even multimodal molecular weight distribution.

Thus we have chosen to use the liquid trichloromethyl chloroformate (diphosgene) which decomposes by temperature yielding phosgene thus to the stoichiometric control can be easily obtained. Due to the need for thermal decomposition higher temperatures are mandatory than in the conventional Fuchs-Farthing method (40-50° C.).

The mechanism of the reaction involves the direct phosgenation of unprotected α-amino acids. Cyclization proceeds through the formation of N-chloroformyl amino acid intermediates and the loss of a second HCl molecule completes the NCA. The reaction generates 2 equivalents of HCl per molecule of NCA. The HCl, as reported above can initiate NCA self-degradation. In this invention limonene was incorporated to the reaction mixture. The limonene is incorporated to scavenge HCl by addition to its double bonds. Amines or other strong bases cannot be used due to the fact that they would attack the formed NCA and lead to its decomposition. In contrast limonene acts as an almost non-nuclephilic/-basic HCl scavenger, see the scheme below showing the mechanism of action of limonene.

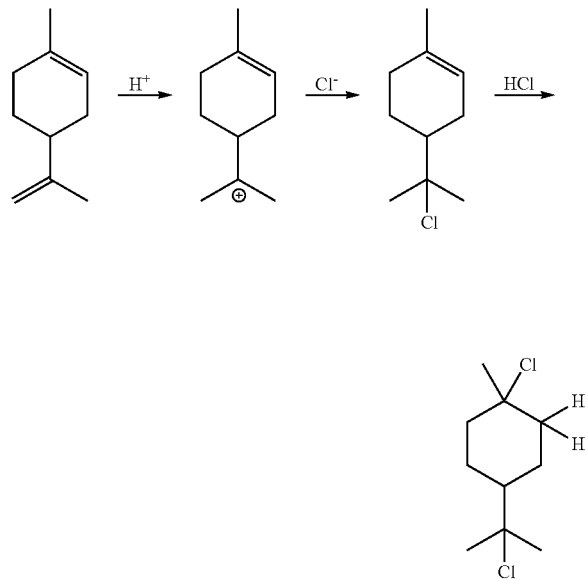

Absence of HCl in the purified NCAs was confirmed by means of a silver nitrate solution. The presence of HCl can be identified by the precipitation of silver chloride when some drops of a solution 1M of AgNO$_3$ are added to a solution of the monomer. The purity of the NCA is the main criteria to ensure long term storage. This issue was corroborated with stability studies of the NCA under different storage conditions. The results are shown in the table below where a "−" symbol means the monomer was found already polymerized/degraded, whereas "+" means monomer was found to be stable.

TABLE 3

Stability of NCA under different storage conditions

| Storage Conditions | Storage Time | | | | | | | |
|---|---|---|---|---|---|---|---|---|
| | 5 d | 6 d | 7 d | 8d | 10 d | 11 d | 20 d | 50 d |
| R.T | − | − | − | − | − | − | − | − |
| R.T/Ar | +/− | − | − | − | − | − | − | − |
| 4° C. | + | + | +/− | − | − | − | − | − |
| 4° C./Ar | + | + | + | + | + | + | +/− | +/− |
| −23° C. | + | + | + | + | + | + | + | + |
| −23° C./Ar | + | + | + | + | + | + | + | + |

R.T: Room Temperature

Thus, monomers were stored at −23° C. under inert atmosphere prior to the polymerization.

Detailed Experimental Approach.

H-L-Glu(OBzl)-OH (17 g, 71.66 mmol) was added to a two-neck 250 mL round bottom flask fitted with a stirrer bar, reflux column, dropping funnel and an argon in and outlet. The apparatus was purged with Ar for 5 min. Afterwards THF (120 mL, anhydrous) was added and the contents were heated to 60° C. Limonene (11.6 mL, 71.66 mmol, 1 Eq) was added to the stirring suspension before diphosgene (5.2 mL, 8.5 g, 43 mmol, 0.6 Eq) dissolved in THF (10 mL, anhydrous) was added via a dropping funnel over a period of 10 min. The reaction was left stirring for 2 hours at 60° C. whilst purging with Ar leading to a clear solution. The reaction mixture was bubbled with Ar to aid the removal of remaining HCl for 2 hours whilst the Ar outlet was directed through an aqueous 1M sodium hydroxide solution to neutralize the gas. The reaction solvent was reduced to a quarter of the original volume by rotary evaporation and ethyl acetate (32 mL) was added. The contents were added to ice cold hexane (200 mL) to form a white precipitate, which was isolated by vacuum filtration and washed with cold hexane.

The solid was recrystallized from toluene (50 mL, anhydrous) and THF (30 mL, anhydrous) under inert atmosphere (N2 or Ar) by using a 250 mL two neck-flask 250 round bottom flask fitted with a stirrer bar, reflux column and an argon inlet and outlet where crystallization was induced by a dropwise addition of cold hexane (27 mL). The solution was stored for one hour at 4° C., and then at −20° C. overnight. Finally the white crystals were filtered under Ar conditions by using schlenck techniques, and stored at −20° C.

To ensure that residual HCl had been successfully removed, NCA (2-4 mg) was dissolved in THF (0.5 mL) and added to a 1M silver nitrate solution (1 mL) where the solution remained clear. When the Ag+ and Cl− ions meet they form the colorless insoluble AgCl salt, which can be easily detected. Another test is checking the solubility in THF. The NCA is soluble in THF, if turbidity is seen in the solution, can be due to the presence of remaining hexane and should disappear by heating the solution, but if precipitation is seen is due to the presence of polymer or starting material (both not soluble in THF).

Yields: 70-80%. Melting point: 93.4° C. Molecular formula: $C_{13}H_{13}NO_5$. Benzyl 3-(2,5-dioxooxazol-4-il)propanoate Molecular Weight: 263.25 g/mol $^1$H NMR (300 MHz, CDCl3) δ7.29 (m, 5H), 6.84 (s, 1H), 5.07 (s, 2H), 4.32 (t, J=6.2 Hz, 1H), 2.52 (t, J=7.0 Hz, 2H), 2.31-1.94 (m, 2H). $^1$H-NRM spectra of pure final product is shown in FIG. 1.

General Method for the Preparation of BF4-Salts.

Synthesis of Tetrafluoroboran n-Butylammonium Salt.

Butylamine (200 mg, 2.7 mmol) was dissolve in 0.1 mL diethylether, and 442 mg (2.7 mmol) of tetrafluoroboric acid diethyl ether complex, HBF4.Et2O, was added to the solution leading to the formation of a white solid Salt in a quantitative yield. The product was then filtered off and recrystallized two times from ethylacetate. The product was then dried under high vacuum and stored at −20° C. Yield: 50% of a white solid. 1H NMR (300 MHz, DMSO) δ 7.58 (s, 3H), 2.84-2.71 (m, 2H), 1.56-1.43 (m, 2H), 1.39-1.25 (m, 2H), 0.89 (t, J=7.3 Hz, 3H). 13C-NMR (300 MHz, DMSO-d6) δ=38.64, 29.09, 19.08, 13.49. EA: C: 29.61% (calc.: 29.85%), H: 7.27% (calc.: 7.51%), N: 8.60% (calc.: 8.70%).

Synthesis of Tetrafluoroboran Neopentylammount Salt.

To 5 ml (5.59 g, 36.74 mmol) of tetrafluoroboric acid diethyl ether complex, $HBF_4(Et_2O)$, 4.31 ml (3.20 g, 36.74 mmol) of neopentylamine were slowly added. The addition resulted in the precipitation of a slightly red solid. The ether was removed under vacuum and the solid was recrystalized two times from ethylacetate and washed with cyclohexane. The product was dried under vacuum. Yield: 42% of a white. 1H NMR (300 MHz, DMSO) δ=7.58 (s, 3H), 2.63 (s, 2H), 0.93 (s, 9H), 13C NMR (300 MHz, DMSO) δ=49.94, 30.21, 26.78 EA: C: 34.35% (calc.: 34.43%), H: 7.99% (calc.: 8.06%), N: 8.07% (calc.: 8.00%).

Synthesis of Tetrafluoroboran PEGammonium Salts.

MeO-PEG(2000)-amine (600 mg, 0.3 mmol, 1892 g/mol) was dissolve in 3 mL of THF, and 53.4 mg (0.3 mmol, 45 μL) of tetrafluoroboric acid diethyl ether complex, $HBF_4.Et_2O$, was added to the solution leading to the formation of a yellow salt in a quantitative yield. The solvent was removed in a rotary evaporator. The product was then dried under high vacuum and stored at −20° C. Yield: Quantitative. 1H-NMR (300 MHz, DMSO-d6): δ (ppm): 7.69 (s, 3H), 3.78-3.70 (m, 2H), 3.52 (d, J=5.4 Hz, 139H), 3.47-3.39 (m, 6H), 3.24 (s, 3H), 3.06-2.91 (m, 2H).

General Procedure for NCA Polymerization. Synthesis of Poly-y-Benzyl L-Glutamate Under $N_2$ Conditions by Using Schlenk Techniques.

y-Benzyl L-Glutamate N-Carboxyanhydride (0.5 g, 1.9 mmol, Mw=264 g/mol) was added to a Schlenk tube fitted with a stirrer bar, a stopper and purged with 3 cycles of vacuum/Ar, under Ar flow and dissolved in 5 mL of the solvent (freshly purified). Afterwards the initiator was added and the mixture was left stirring at 40° C. in an oil bath for 3 days under Ar/N2 atmosphere with constant pressure. After 3 days reacting the solution was poured in 40 mL of cold diethyl ether leading to a white suspension that was centrifugated at 4.000 rpm during 10 minutes. The supernatant was removed and the white solid was then suspended in milllQ water and freeze-dried.

1H NMR (300 MHz, DMF) δ 8.58 (s, 1H), 7.42 (s, 5H), 5.19 (s, 2H), 4.21 (s, 1H), 2.81 (s, 2H), 2.45 (s, 2H). 13C NMR (101 MHz, DMF) δ 175.94 (s), 172.26 (s), 162.77-162.18 (m), 161.98 (s), 136.76 (s), 128.87-127.75 (m), 66.05 (s), 57.13 (s), 35.41-34.17 (m), 32.48 (s), 30.84, 30.30-29.04 (m), 27.28 (s), 25.99 (s).

*Note: the corresponding signals of the initiator depend on the initiator used: nButylammonium; neopentylammonium; metoxypolyethylenglicolammonium NCA Polymerization Kinetics.

y-Benzyl L-Glutamate N-Carboxyanhydride (0.6 g, 2.27 mmol, Mw=264 g/mol) was dissolved in 6 mL of previously purified DMF. The content was split into 6 slenchk tubes fitted with a stirrer bar, a stopper, and under $N_2$ atmosphere. Afterwards, a solution in DMF of the initiator was prepared, and the corresponding amount was added to each tube. The mixtures were left stirring at 40° C. in an oil bath for 4 days under Ar/$N_2$ atmosphere with constant pressure. Time points of the kinetics were collected each 14, 22, 38, 46, 70, and 96 hours, by precipitation of the polymers into diethyl ether tree times, freeze-dry of the sample in water and GPC analysis of the molecular weight eluting with DMF/LiBr.

As example Table 3 displays some of the results obtained in different polymerizations with several BF4-initiators, two of them small initiators n-butylammonium tetrafluoroboran and neopentylammonium tetrafluoroboran leading to homopolymer of y-benzyl-glutamic acid; and one macroinitiator based on PEG (polyethylenglycol) of M.W. ~near to 2.000 and PDI: 1.03, leading to diblock copolymers PEG-Poly(y-benzyl-glutamic acid). The neopentylammonium tetrafluoroboran initiator was used in replacement of n-butylamine in order to facilitate the corresponding assignment of DP by 1H NMR. This is due to the presence of 9 chemically equivalent protons in the initiator (three metil $CH_3$— groups) which leads to an increase in the sensitivity of the characterization of the polymer by $^1$H-NMR spectra. [P: Polymer M]/[I]: Monomer to Initiator ratio; DP: Degree of polymerization (% of [M]/[I]) Mw: weight average molecular weight; Mn: number average molecular weight index (ratio Mw/Mn that gives a measure of the dispersity D).

$$DP = \frac{[M]}{[I]} \cdot conv$$

TABLE 3

NCA Polymerization in DMF with n-Butylammonium tetrafluoroborate, and with n-PEG(2000)ammonium tetrafluoroborate as initiator at 40° C.

| Initiator | [M]/[I] | DP$_{(calc.)}$ | DP $^1$H-NMR | [M] Mol/L | Reaction Time (d) | Yield (%) | Mn (KDa) | Mw (KDa) | PDI |
|---|---|---|---|---|---|---|---|---|---|
| N-Butyl- | 50 | 32 | 29 | 0.38 | 3 d | 64 | 6.7 | 7.4 | 1.1 |
| ammonium | 100 | 64 | 60 | 0.38 | 3 d | 64 | 13.8 | 15.2 | 1.1 |
| BF$_4$ salt | 200 | 126 | 107 | 0.38 | 3 d | 63 | 16.1 | 17.7 | 1.2 |
|  | 300 | 147 | 143 | 0.38 | 3 d | 49 | 20.7 | 23.5 | 1.1 |
|  | 400 | 288 | 212 | 0.38 | 3 d | 72 | 31.6 | 37.9 | 1.2 |
|  | 800 | 424 | — | 0.38 | 3 d | 53 | 48.4 | 63.0 | 1.2 |
|  | 1600 | 816 | — | 0.38 | 6 d | 51 | 94.4 | 112.2 | 1.2 |
| Neopentyl | 50 | 40 | 43 | 0.38 | 3 d | 80 | 7.1 | 8.6 | 1.2 |
| Ammonium | 100 | 81 |  | 0.38 | 3 d | 81 | 14.4 | 18.7 | 1.2 |
| BF$_4$ salt | 200 | 176 | 105 | 0.38 | 3 d | 88 | 17.86 | 22.31 | 1.2 |
|  | 500 | 440 | 322 | 0.19 | 3 d | 88 | — | — | — |
|  | 1200 | 960 | — | 0.38 | 3 d | 80 | 156.5 | 191.1 | 1.2 |

TABLE 3-continued

NCA Polymerization in DMF with n-Butylammonium tetrafluoroborate, and with n-PEG(2000)ammonium tetrafluoroborate as initiator at 40° C.

| Initiator | [M]/[I] | $DP_{(calc.)}$ | DP $^1$H-NMR | [M] Mol/L | Reaction Time (d) | Yield (%) | Mn (KDa) | Mw (KDa) | PDI |
|---|---|---|---|---|---|---|---|---|---|
| PEG(2000) | 50 | 36 | 38 | 0.38 | 3 d | 73 | 7.0 | 9.4 | 1.2 |
| Ammonium | 100 | 81 | 79 | 0.38 | 3 d | 81 | 13.9 | 18.1 | 1.2 |
| $BF_4$ salt | 200 | 160 | 148 | 0.38 | 3 d | 80 | 18.4 | 24.7 | 1.2 |

Enclosed in FIG. 2, $^1$H-RMN spectra of n-butil tetrafluoroborane salt polymerizations at varying proportions of [M]/[I] ratio in DMF; FIG. 3 represents ([M]/[I] ratio relative to the Mn obtained by GPC and FIG. 4

With DMF as a solvent monomodal distributions with very low polydispersities to low in other cases were obtained in the NCA polymerization technique using tetrafluoroborate salts. Following the optimization process, the effect of the temperature was also studied. From the literature mentioned in the introduction, it is already known that lower temperatures suppress some side reactions but elongates reaction times. As in the process of optimization the time was kept as a constant parameter, when the reactions were done at lower temperature, lower yields were obtained (20-30%). Higher temperatures (60, and 80° C.) resulted in slightly yellow coloured reactions in the case of 60° C., and strong yellow coloured with 80° C., which can be explained by the decomposition of DMF into dimethylamine and the cleavage of the protecting group at high temperatures, leading to benzyl alcohol, which is yellow coloured. In conclusion, a lack of control is present when high temperatures like 60° C. or above are applied in the polymerization. When low temperatures are applied, very poor yields are obtained (if three days of reaction time are kept). That is why optimal temperature was set at 40° C. for DMF or ranging from 5-40° C. with DMI. Parameters such as concentration of the reaction media where optimized similarly, setting 0.38M as the optimal concentration relative to the monomer in the case of DMF. It is a requirement to work in a range of concentrations to avoid less defined polymers.

To test whether this methodology could be applicable to every initiator, different initiators based in $BF_4$ salts were used, as propargyl$NH_3BF_4$ and $N_3EG(2)$ $NH_3BF_4$. The use of these salts as initiators will provide polymers with alkyne and azide moieties respectively in the C-terminus of the polymer, which could be used for bioconjugation afterwards. The following table summarizes the results obtained with the different initiators.

TABLE 4

NCA polymerization with different tetrafluoroborate salts as initiator at 40° C. during 3 days varying in THF as well as in DMF [monomer/initiator] = 200

| Initiator | P | DP (calc.) | DP ($^1$H-NMR) | [C] M | t (d) | Yield (%) | Mn by GPC (KDa) | Mw By GPC | PDI |
|---|---|---|---|---|---|---|---|---|---|
| ~~~NH$_2$·HBF$_4$ | 9 | 126 | 107 | 0.38 | 3 | 63 | 16.1 | 17.7 | 1.2 |
| (CH$_3$)$_3$C-NH$_2$·HBF$_4$ | 16 | 176 | 105 | 0.38 | 3 | 88 | 17.86 | 22.31 | 1.2 |
| ~O(CH$_2$CH$_2$O)$_{42}$~NH$_2$·HBF$_4$ | 20 | 160 | 148 | 0.38 | 3 | 80 | 18.4 | 24.7 | 1.2 |
| HC≡C-CH$_2$-NH$_2$·HBF$_4$ | 21 | 168 | — | 0.38 | 3 | 84 | 16.5 | 22.1 | 1.3 |
| N$_3$~(O~)$_2$O~NH$_2$·HBF$_4$ | 22 | 154 | — | 0.38 | 3 | 77 | 18.3 | 24.5 | 1.3 | a) Note, in the case of EG, PEG and propargylammonium initiators, the DP cannot be extracted from the $^1$H-NMR spectra because the corresponding signals are overlapped with the water signal.

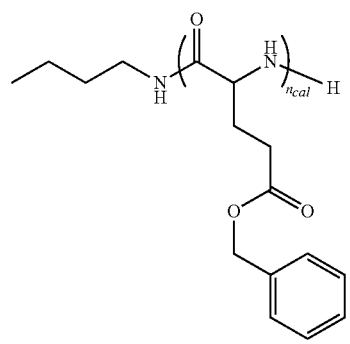

| $n_{cal}$: | P: |
|---|---|
| 50 | 7 |
| 100 | 8 |
| 200 | 9 |
| 300 | 10 |
| 400 | 11 |
| 800 | 12 |
| 1600 | 13 |

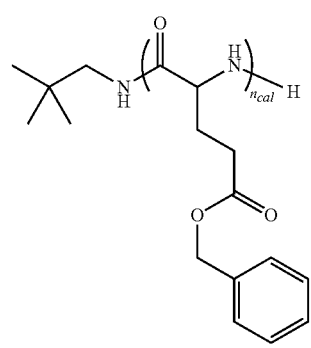

| $n_{cal}$: | P: |
|---|---|
| 50 | 14 |
| 100 | 15 |
| 200 | 16 |
| 1200 | 17 |

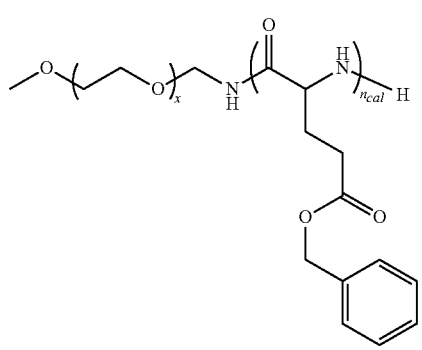

| $n_{cal}$: | P: |
|---|---|
| 50 | 18 |
| 100 | 19 |
| 200 | 20 |

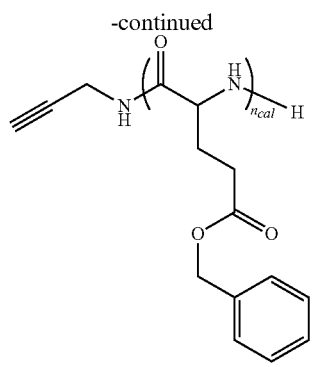

| $n_{cal}$: | P: |
|---|---|
| 200 | 21 |

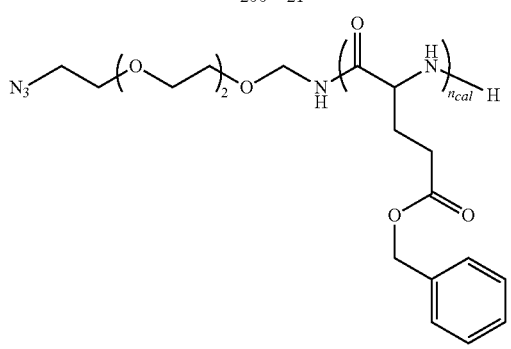

| $n_{cal}$: | P: |
|---|---|
| 200 | 22 | n represents number of γ-benzyl-glutamate units in the polymer, from 1 to 1000

Figure 5:
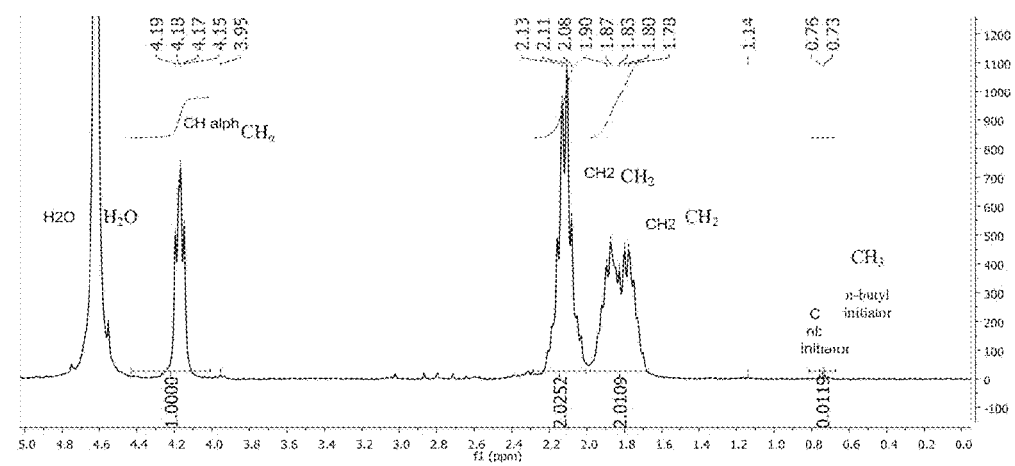

The approximate quantity used for each polymerization ranges from 0.5-1 grams of monomer. To validate the possibility of an industrial application of the reaction, and taking into account that the polyglutamic acid is supposed to be the polymeric base of different polymer-drug conjugates the synthesis was scaled up. Thus, once all these promising preliminary results were obtained, the reaction was scaled up four times to 5 grams by using the optimized conditions. In all cases the PDI of the polymers obtained was 1.2-1.3 and a yield between 80-90% with Molecular weights Mn: 31.47 KDa, PDI:1.26, ([M]/[I]=333); Mn:26.06 KDa, PDI:1.27, ([M]/[I]=300); Mn: 15.23 KDa PDI:1.18 ([M]/[I]=200) and Mn: 7.08 KDa PDI:1.19, ([M]/[I]=50) respectively as determined by GPC. FIG. 5 includes $^1$H-NMR spectra of n-butil-α-polyglutamic acid corresponding to scale up of 5 grams of one of the batches after deprotection, DP=252 can be confirmed by NMR.

General Methods for the Deprotection of Poly(γ-Benzyl-L-Glutamate)

Three different methodologies to remove benzyl protecting groups were studied. The first of them consist on the use of an acidic medium such as HBr/TFA, the second by using sodium hydroxide in a mixture of THF/water at low temperature, and the third by using hydrogen reducing atmosphere with Pd(OH)/C as a catalyser. All three methods gave rise to complete deprotection of benzyl group, however, the third of the options herein exposed is restricted to polyglutamates with molecular weights below 10 kDa, it also requires of an additional step to remove the catalyser leaving to reduced yields. Polymers were characterized using $^1$H-NMR and polarimetry until constant values ~0.6 were achieved.

Deprotection of Poly(γ-Benzyl-L-Glutamate) with Hbr in Trifluoroacetic Acid.

100 mg (0.0035 mmol, Mw: 28251 g/mol) of Poly(γ-benzyl-L-glutamate) were dissolved in 3 mL of trifluoroacetic acid (TFA) in a round botton flask fitted with a stopper and a stirring bar. Afterwards, 150 mg of HBr 48% were added (0.91 mmol, 2 equivalents per carboxyl group), and the yellow mixture was left stirring for five-eight hours.

Then, the solution was poured into a large excess of diethyl ether leading to a white solid that was centrifugated removing the white solution. The product was washed three times with diethyl ether. After that, the product was then purified by acid-base precipitation (NaHCO3/HCl 6M). Dyalisis was done leading to the sodium salt form. Finally, to get the acid form, the product was then precipitated at pH 3 by adding drops of HCl 6M. Yield: quantitative 1H NMR (300 MHz, D$_2$O) δ: 4.31-4.26 (m, 1H), 2.38-2.14 (m, 2H) 2.10-1.80 (m, 2H)

purging with H$_2$. The reaction was left stirring for two days under H$_2$ atmosphere (with a balloon full of H$_2$). The purification was carried out pouring the solution into a large excess of diethyl ether. Centrifugation leads to a mixture of a white solid with palladium/charcoal. The solid was redissolved in acidic water and filtered through a celite column in a syringe and a filter. As a result, PGA was obtained as a white powder. Yield: 40%.

Versatile Architectures (Diblock and Triblock Systems)

Synthesis of Benzyl-Protected Triblocks (TBs) PEG-PGA-PEG

Triblock systems (TB) were obtained by means of the reaction between the PEG-PGA diblocks (DB) (previously obtained using n-PEG(2000)ammonium tetrafluoroborate as initiator) and NHS-activated PEG. General method is explained in detail below:

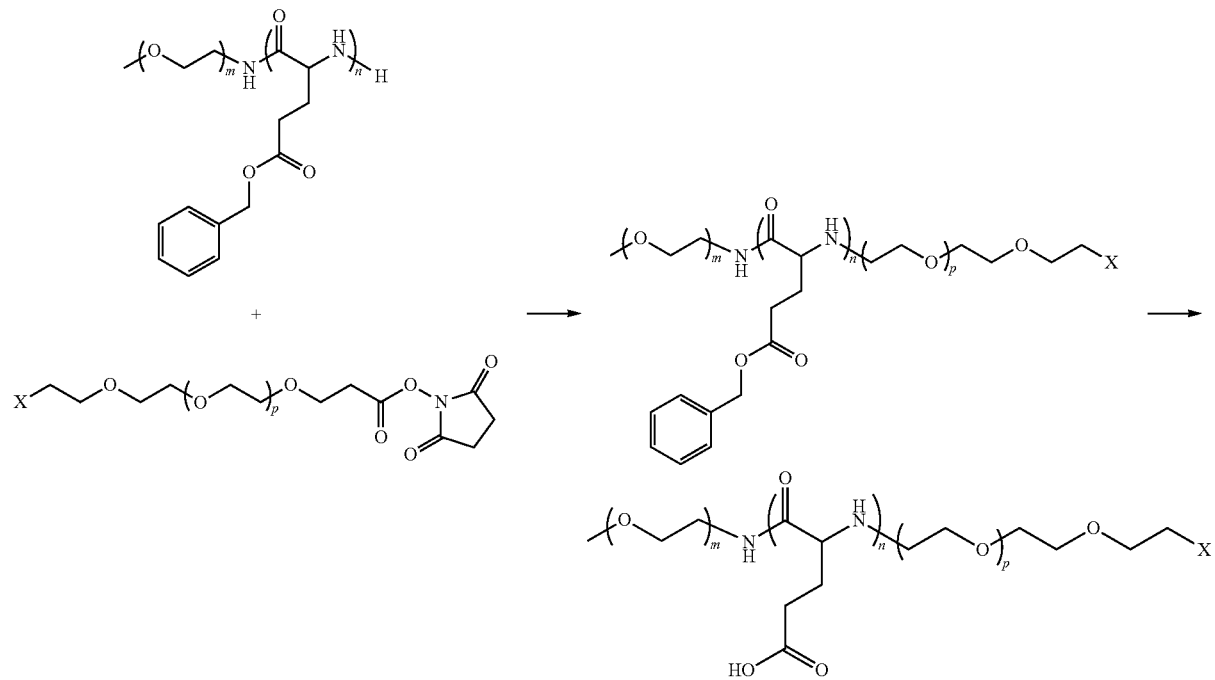

Deprotection of Poly(γ-Benzyl-L-Glutamate) with NaOH in THF/H$_2$O 100 mg (0.0035 mmol, Mw: 28251 g/mol) of Poly(γ-benzyl-L-glutamate) were dissolved in 7 mL of THF at 4° C. Then, sodium hydroxide (27.36 mg, 0.684 mmol) dissolved in 1 mL of H$_2$O was added dropwise to the polymer solution and was stirring vigorously during 16 h. Solution was then neutralized with acetic acid, THF evaporated under vacuum and the resulting polymer purified directly by dialysis. Yield, quantitative. $^1$H-NMR (300 MHz, D$_2$O) δ: 4.31-4.26 (m, 1H), 2.38-2.14 (m, 2H) 2.10-1.80 (m, 2H)

Deprotection of Poly(γ-Benzyl-L-Glutamate) Reducing with Pd(OH)$_2$ Charcoal in DMF.

100 mg (0.0035 mmol, Mw: 28251 g/mol) of Poly(γ-benzyl-L-glutamate) were dissolved in 15 mL of N,N-dimethylformamide (DMF) absolute, in a round bottom flask fitted with a septum and a stirring bar. Then Palladium/Charcoal was added and the flask was purged with N$_2$ in order to remove the air. Afterwards the N$_2$ was removed by wherein:

X represents an alkyl group, Defined C-terminal attachment group (alkyne, azyde, thiols, halides, activated thiols, alkenes, activated esters, activated alcohols, protected amines, maleimide groups, acetals, activated carboxylic acids)

m represents number of ethylenglycol repeating units in the polymeric fragment PEG used as a first block, from 1 to 500 n represents number of repeating units of y-benzyl glutamate of the peptidic block, 1 to 1000 p represents number of ethylenglycol repeating units in the polymeric fragment PEG used as a third block, from 1 to 500

Briefly for TB50, 750 mg (0.058 mmol, MW 12854) of DB50 were dissolved in anhydrous CH$_2$Cl$_2$, the pH was adjusted to 8.0 with DIEA and 209 mg (0.104 mmol, MW 2007) of mPEG-NHS were added. The reaction proceeded overnight under stirring, then the product was purified by extractions, first with NaOH 0.1N, then with saturated NaCl solution and finally with HCl 0.1N. The organic phase was collected, dried with Na₂SO₄, filtered, concentrated under vacuum and precipitated in cold diethyl ether. After 2 h at −20l, the precipitated polymer was filtered, washed and dried under vacuum.

TB100, TB200, TB400 and TB800, were obtained following the same methodology with the quantities and yields shown in Table 5 that follows:

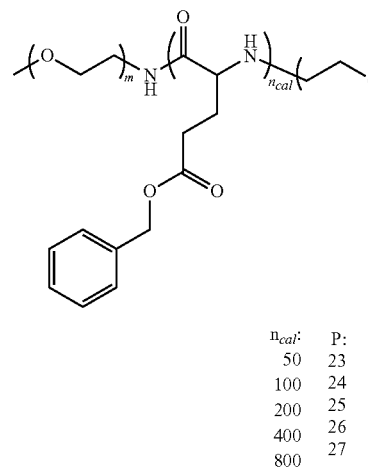

| $n_{cal}$: | P: |
|---|---|
| 50 | 23 |
| 100 | 24 |
| 200 | 25 |
| 400 | 26 |
| 800 | 27 |

TABLE 5

| | REACTION | | |
|---|---|---|---|
| PRODUCT | P | mg DB/mmol | mg PEG/mmol | Yield (%) |
| TB50 | 23 | 750/0.058 | 209/0.104 | 90% |
| TB100 | 24 | 520/0.022 | 78/0.039 | 85.5% |
| TB200 | 25 | 1572.4/0.034 | 123/0.061 | 96% |
| TB400 | 26 | 560/0.0062 | 22.3/0.011 | 88% |
| TB800 | 27 | 1260.2/0.0071 | 25.4/0.0126 | 82% |

The products were characterized by gel permeation chromatography (GPC) and nuclear magnetic resonance ($^1$H-NMR) in CDCl₃.

Following, TB50 was solved in 5-7 ml of TFA, then HBr 48% w/v in acetic acid was added and the reaction proceeded overnight. Then the polymer was precipitated in cold diethyl ether and after 2 hours at −20° C., the precipitate was recovered by centrifugation at 4000 rpm for 10 minutes at 4° C. an d dried under vacuum.

| $n_{cal}$: | P: |
|---|---|
| 50 | 28 |
| 100 | 29 |
| 200 | 30 |
| 400 | 31 |
| 800 | 32 |

TABLE 6

| | REACTION | | |
|---|---|---|---|
| PRODUCT | P | mg DB/mmol | ml HBr/mmol | YIELD (%) |
| TB50d | 28 | 735/0.05 | 1.686/10 | 90% |
| TB100d | 29 | 444/0.017 | 1.146/6.8 | 95% |
| TB200d | 30 | 1503.5/0.031 | 4.256/6.31 | 90% |
| TB400d | 31 | 481.7/0.0053 | 1.42/8.42 | 90% |
| TB800d | 32 | 949.2/0.0053 | 2.858/16.9 | 90% |

The products were characterized by GPC and $^1$H-NMR in de-DMSO.

Finally, part of the deprotected TBs co-polymers was solved in a calculated amount of sodium bicarbonate and 2-3 ml of water. Once the polymers were solubilized, the solution was loaded in G25 column and eluted with milliQ H₂O, collecting 50 fractions of 3 ml each, a part the first two, that were of 10 ml. The fractions were lyophilized and some of the fractions were analyzed by $^1$H-NMR in D₂O.

If an optional functionality at PEG terminus, the tri-block or diblock synthesis is performed by conjugation of a further unit of bi-functional PEG.

As stated above, PEG-PGA or n-BuPGA is obtained reacting NCA-L-Glu-OBn with MeOPEGNH₃BF4 or nBuBF₄. Varying the equivalent ratio monomer:PEG, it is possible to obtain di-block with different amount of glutamic-acid unit (theoretically 200, 400 and 800).

The obtained di-block is in its protected form and the protected groups —OBn are eliminated in a previous step to the linking of the second polymeric block. This second PEG is a bifunctional COOH-PEG-SH that is activated in order to obtain NHS-PEG-SS-4TP. This double activation previous to the linking of the polypeptidic block is performed to asure high yields and avoidance of crosslinking reactions.

This last block confers TB final structure (or DB in the case nBuPGA) an additional semitelechelic linker site capable of conferring specific and selective conjugations to the activated functional group introduced, by formation of disulphide bonds.

Detailed Experimental Protocol
PEG-PGA$_n$-PEG4TP (TB) Synthesis

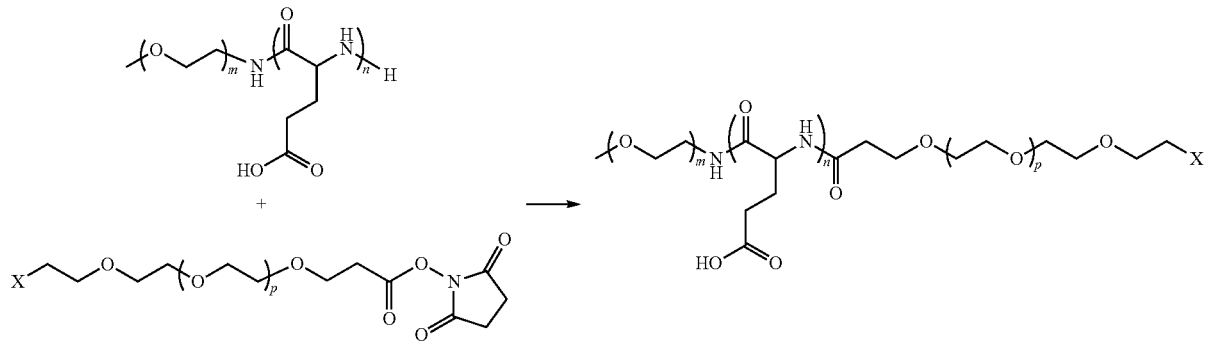

wherein:
X represents an alkyl group, Defined C-terminal attachment group (alkyne, azyde, thiols, halydes, activated thiols, alkenes, activated esters, activated alcohols, protected amines, maleimide groups, acetals, activated carboxylic acids)
m represents number of ethylenglycol repeating units in the polymeric fragment PEG used as a first block, from 1 to 500
n represents number of repeating units of γ-benzyl glutamate of the peptidic block, 1 to 1000
p represents number of ethylenglycol repeating units in the polymeric fragment PEG used as a third block, from 1 to 500

In a 50 ml round bottom flask is placed 1 g of selected DB previously deprotected (as example, with 200 residues of GA; 1 eq; 27,692 g/mol), dissolved in 20 m DMF and purged with $N_2$ atm. 1.3 eq of NHS-PEG-SS-4TP (163.4 mg; 3480 g/mol) is dissolved in anhydrous DMF (3 ml) and purged with $N_2$ before being added to the reaction mixture. The pH is increased till 8 with DIEA (1.5 mL in this example). The reaction is left stirring at RT under $N_2$ atm for 3 days. Thereafter, the flask is kept under vacuum to remove the DMF, the product is dissolved in $NaHCO_3$ 1 M (5 ml) and purified with SEC (Sephadex G25, dd$H_2$O) column. 50 samples of 2 ml (except for the first and second aliquots of 10 ml each) fractions were collected. The fractions were lyophilized and the purified TB recollected for further analysis and conjugation. Characterization by $^1$H-NMR in $D_2$O. (CDCl$_3$, 300 MHz): δ: 2.8-2.9 (4H, t, J=6.3 Hz, H$_6$), δ: 3.3-3.8 (m, H$_{3,4,5}$), δ: 7.4 (4H, d, J=4.5 Hz, H$_2$,2), 8.4 (4H, d, J=4.5 Hz, H$_{1,1'}$).

The SS-4TP group will allow further conjugation with selected moieties including peptides, proteins or antibodies through a disulfide bound. Again, the functionalization yield is assessed with the Ellman assay and/or with 4TP assay. Yield of the procedure is assessed to be around 35%; —SH activation around 90%.

To confirm the percentage of 4TP groups introduced in the conjugation, electrophotometric assays, direct quantification (release of 4TP group) and indirect quantification (using Ellman assay) were performed. Product was stored for future analysis and linking. Yield: 35%, activation 90% as seen in Table 7 bellow.

TABLE 7

| Product | | P | t (d) | 4TP activation (%) | Yield. (%) |
|---|---|---|---|---|---|
| PEG-PGA$_{100}$-PEG4TP | TB100 | 33 | 3 | — | — |
| PEG-PGA$_{200}$-PEG4TP | TB200 | 34 | 3 | 90 | 35 |
| PEG-PGA$_{400}$-PEG4TP | TB400 | 35 | 3 | — | — |
| PEG-PGA$_{800}$-PEG4TP | TB800 | 36 | 3 | — | — |

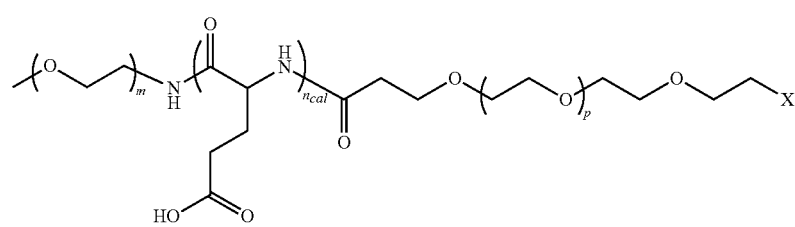

| $n_{cal}$ | P: |
|---|---|
| 100 | 33 |
| 200 | 34 |
| 400 | 35 |
| 800 | 36 | nBuPGA,-PEG4TP (DB) Synthesis

General methodology used for diblock synthesis is described as follows:

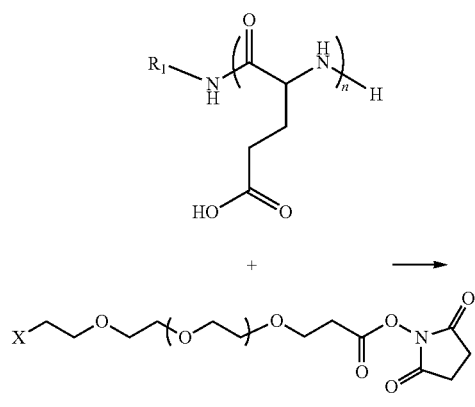

wherein:

R1 represents an alkyl group, for example n-butilamine, neopentil amine; carbonated chain (saturated and/or insaturated) with or without electronegative atoms (i.e. O in PEG-NH$_2$)

X represents an alkyl group with Defined C-terminal attachment group (alkyne, azyde, thiols, halides, activated thiols, alkenes, activated esters, activated alcohols, protected amines, maleimide groups, acetals, activated carboxylic acids)

n represents number of y-benzyl glutamate of the peptide block, form 1 to 1000

In a 50 ml round bottom flask, 100 mg of deprotected nBu-PGA homopolymer with 200 units of glutamic acid (1 g, 258.57 g/mol) is dissolved in 8 mL anhydrous DMF at room temperature and the system was purged with N$_2$. In a vial, 1.5 eq of NHS-PEG-SS-4TP (17 mg; 3357 g/mol) was dissolved in 2 mL of anhydrous DMF and purged with N$_2$ before adding to the reaction flask. pH was adjusted to 8.0 with DIEA and left to stir at room temperature under inert atmosphere for 72 h. Then, the solvent was evaporated under reduced pressure and the residue redissolved in the minimum volume of NaHCO$_3$ 1M and purified with SEC (Sephadex G25, ddH$_2$O). 50 samples of 2 ml (except for the first and second aliquots of 10 ml each) fractions were collected. The fractions were lyophilized and the purified TB recollected for further analysis and conjugation by $^1$H-NMR in D$_2$O.

To confirm the percentage of 4TP groups introduced in the conjugation, electrophotometric assays, direct quantification (release of 4TP group) and indirect quantification (using Ellman assay) were performed. Product was stored for future analysis and linking. Yield: 64%, activation 90% as seen in Table 8 bellow

TABLE 8

| Product | P | t (d) | 4TP activation (%) | Yield (%) |
|---|---|---|---|---|
| nBuPGA$_{100}$-PEG4TP | DB100 | 37 | 3 | 90 | 64 |
| nBuPGA$_{200}$-PEG4TP | DB200 | 38 | — | — | — |
| nBuPGA$_{400}$-PEG4TP | DB400 | 39 | — | — | — |
| nBuPGA$_{800}$-PEG4TP | DB800 | 40 | — | — | — |

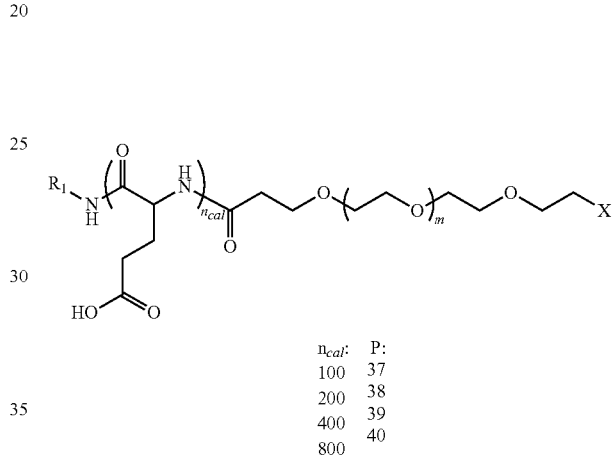

$n_{cal}$: P:
100  37
200  38
400  39
800  40

—SS-4TP functional group will allow, both in TB as in DB-SS-4TP, the subsequent linking of active ligands including peptides, proteins or antibodies by means of a disulphide bond.

Bioconjugation Chemistry

General Method for Labeling with Oregon Green Cadaverine.

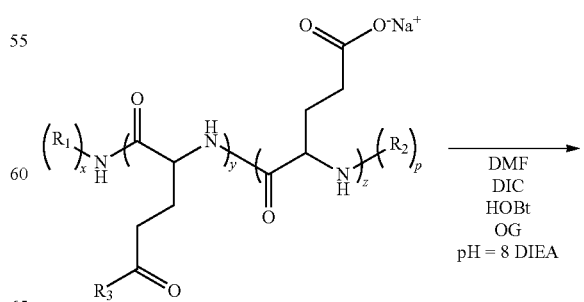

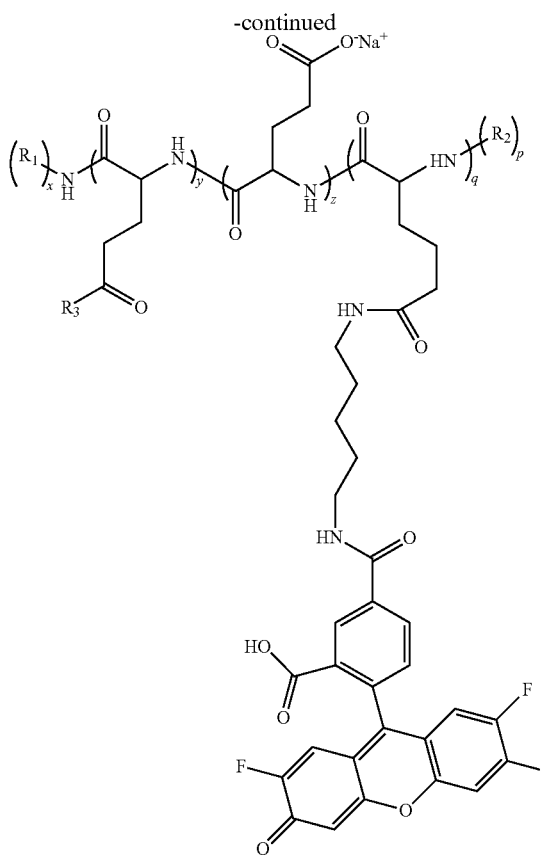

wherein:
R1 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol).

R2 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol), PEG-thiol, PEG-4TP.

R3 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from n=2 to n=16); amino acids such as lysine, arginine, imidazole, histidine and cysteine, and secondary and tertiary amino groups.

x represents number of monomer units into definition R1, from 1 to 500 y represents number of glutamic units modified with R3 In the polymer, from 1 to 500 z represents number of glutamic units not modified in the polymer, from 1 to 1000 p represents number of monomer units included into R3 definition, from 1 to 500

In a round two necked bottom flask fitted with a stirrer and two septums, 29 mg of polyglutamic acid (0.225 mmol GA units, 1 eq) was weighted and dissolved in 1.5 mL of dry DMF under $N_2$ flow. 1,12 μL of N,N'Diisopropylcarbodiimide, DIC (0.85 mg, 0.00674 mmol, d=0.806 g/ml, Mw=126 g/mol 0.03 eq) was added and the reaction was left to proceed for 5 minutes. After that 1 mg (0.00674 mmol, Mw=135.1 g/mol 0.03 eq) of Hydroxybenzotriazole, HOBt was added in solid form. The reaction was then left to proceed for 10 minutes more. Afterwards 1 mg (2.01.10-3 mmol, Mw=496.47 g/mol, 0.0089 eq) of Oregon Green Cadaverine was added. The pH was adjusted to 8 by adding ~100 μL of DIEA. The mixture was left stirring overnight protected from light. Finely, the solvent was removed in the vacuum pump and the product was dissolved in 300 μL of water by adding ~50 μL of 1M $NaHCO_3$ and purified by Sephadex G25/PD10 column in millQ water. The Oregon Green loading was calculated by fluorescence spectroscopy by registration of the fluorescence in al the fractions collected from the column. General Labelling efficiency. 80-90%. Yield: 80-85%

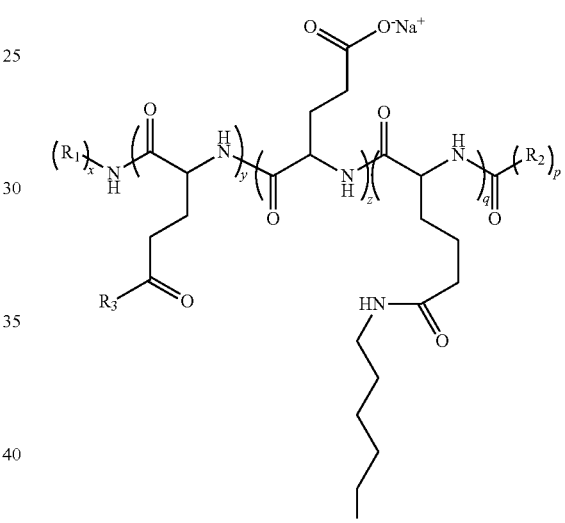

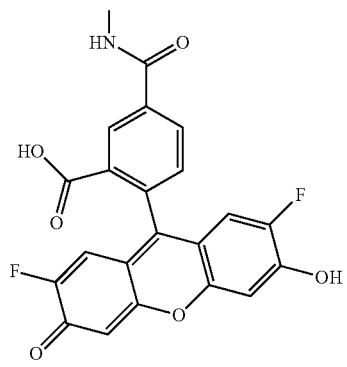

| $n_{cal}$: | P: |
|---|---|
| 50 | 41 |
| 100 | 42 |
| 200 | 43 |
| 400 | 44 |
| 800 | 45 |

General Methodology for Labelling with Cyane5.5.

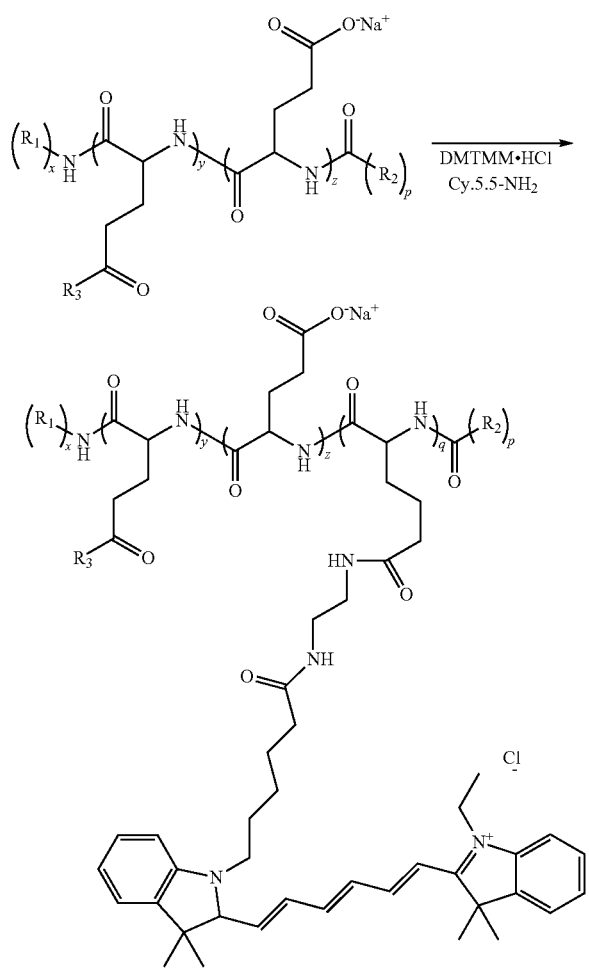

wherein:
R1 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol).

R2 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol), PEG-thiol, PEG-4TP.

R3 represents an alkyl group with Defined C-terminal attachment group (alkyne, azyde, thiols, halides, activated thiols, alkenes, activated esters, activated alcohols, protected amines, maleimide groups, acetals, activated carboxylic acids), ethylenglicol (EG) of different molecular weights including polyethylenglicol (PEG, from n=2 to n=16); amino acids such as lysine, arginine, imidazole, histidine and cysteine, and secondary and tertiary amino groups.

x represents number of monomer units into definition R1, from 1 to 500 y represents number of glutamic units modified with R3 in the polymer, from 1 to 500 z represents number of glutamic units not modified in the polymer, from 1 to 1000 p represents number of monomer units included into R3 definition, from 1 to 500

In a two bottle-neck round bottom flask 59.6 mg of DB200 (0.355 mmol COOH) were dissolved in 8 mL of ddH$_2$O and left stirring. In a separate vial, 3.8 mg of Cy5.5-NH$_2$ (1.8% mol, Mw=588.36 g/mol) were dissolved in 13 mL de ddH$_2$O which were then added to the reaction. Following, 2.9 mg of DMTMM-HCl (Mw=276.72 g/mol, 1.5 eq) were added to the reaction. The mixture was left stirring for 48 h protected from light at room temperature and under inert atmosphere. The reaction was monitored by thin layer chromatography (methanol:acetic acid). Finally the solvent was evaporated under reduced pressure and the residue dissolved in 300 □L of water. Then purified by SEC(Sephadex G25/PD10) in milliQ water as eluent. Cy5 charge was determined by fluorimetry ($\lambda$exc. 598 nm, $\lambda$em 655 nm) monitoring the signal of each fraction of the column. General efficiency of labelling: 90.86% (1.63% mol Cy5.5). Yield of the reaction: 60%

Post-Polymerization Modification of Polyglutamic Acid (PGA) by Acid/Base Chemistry.

Post-polymerization modification can be an attractive approach for the synthesis of functional polymers overcoming the limited functional group tolerance of many controlled polymerization techniques. Due to all the advantages of the above described methodology of NCA polymerization, the exploration of the post-polymerization modification of the well-defined polyglutamates was explored with a view to the incorporation of functionalities for side specific conjugation.

For that purpose, the PEGylatlon of PGA as well as the incorporation of propargylamine and amino-PEG-azide was performed. On one hand, the PEGylation is well known as the process of covalent attachment of PEG polymer chains to another molecule, normally a drug or therapeutic protein. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. PEGylation can also provide water solubility to hydrophobic drugs and proteins. Therefore, the introduction of PEGylated units into the polymer backbone not only will allow us the inclusion of a spacer between the polymer and the corresponding bioactive compound, but also can modify the in vivo behaviour, biodistribution and therapeutic application. On the other hand, the azide and alkyne modification were chosen to have suitable moieties for a click chemistry attachment of the corresponding bioactive compound with all the benefits that this kind of reactions lead as pointed out in the introduction.

General Method for Post-Polymerization Modification Techniques.

In a round one neck bottom flask fitted with a stirrer and a stopper, 200 mg of polyglutamic acid (1.55 mmol unit of Glutamic Acid, 1 eq) were suspended in 10 mL of milliQ water. Afterwards 128.7 mg (0,465 mmol, 0.3 eq) of DMT-MMCl$^-$ was added dissolved in 5 mL of milliQ water. After 10 minutes (0.93 mmol 0.6 eq) of the corresponding amine were added and the pH was adjusted to 8 by adding some drops of 1M NaHCO$_3$ solution. The reaction was allowed to proceed over night stirring at room temperature. After this, as all by products are water soluble, either ultrafiltration (with a membrane of 3.000 Mw), size exclusion chromatography with Sephadex G25 columns, was done in order to purify the copolymer or acid/base precipitation. A colorless amorphous solid was yielded after freeze-drying the sample.

Yield: 80-90%. $^1$H-NMR Propargyl modified PGA (300 MHz, D$_2$O) δ: 4.30-4.02 (m, 1H), 3.81 (s)*, 2.48 (s)*, 2.35-2.02 (m, 2H), 2.01-1.65 (m, 2H). $^1$H-NMR PEG-azide modified PGA (300 MHz, D$_2$O) δ: 4.28-4.07 (m, 1H), 3.65-3.51 (m)*, 3.48 (t, J=5.6 Hz)*, 3.40-3.30 (m)*, 3.25 (d, J=4.9 Hz)*, 2.29-2.00 (m, 2H), 1.98-1.65 (m, 2H). $^1$H-NMR PEG-OMe modified PGA (300 MHz, D$_2$O) δ: 4.33-4.19 (m, 1H), 3.95-3.78 (m)*, 3.77-3.49 (m)*, 3.34 (s)*, 2.41-1.76 (m, 4H)

*The number of corresponding H, depends on the percentage of functionalization of the polymer backbone.

Post-Polymerization Modification with Propargylamine.

The post-polymerization modification of PGA with propargylamine was performed as reported by "K. Thompson, S. Michelsen. J. Poly. Sci.: Part A: Poly. Chem. 2006, 44, 126-136" with slight modifications. The activation of the carboxylic acids within the polymer backbone of PGA was carried out by using 4-(4,6-Dimethoxy-1,3,5-triazin-2-yl)-4-methyl morpholinIum chloride (DMTMMCl$^-$). Afterwards, propargylamine was added into the reaction mixture leading to the corresponding alkyne modified polymer. The mechanism of action of DMTMMCl$^-$ is showed below, and consists in the formation of the corresponding activated ester with the release of 4-methylmorpholine in a first step. This activated ester reacts with the corresponding amine compound by adjusting the pH of the reacting mixture to 8 in order to favor the amine form of the compound instead of the protonated one that coexist in equilibrium, with non nucleophilic character, see scheme below:

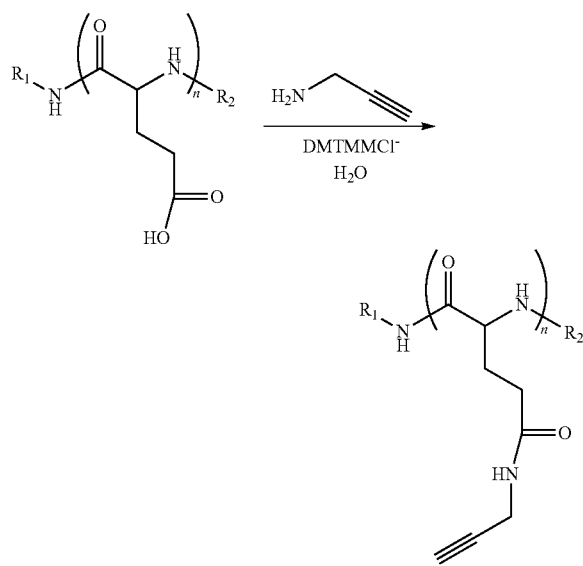

wherein, n represents number of glutamic units, from 1 to 1000 x represents number of units of glutamic modified with propargylamine, from 1 to 1000

The reaction was left to proceed for 16 hours, and different procedures for the purification of the resulting compound were explored:

a) One of them is acid/base precipitation since PGA is insoluble when it is as carboxylic acid form, and soluble when it exists as sodium salt form. Therefore, as all by-products were water soluble, the resulting polymers were purified by precipitation in acidic water (pH-3-4) and redi-solution by basification with sodium bicarbonate. The process was repeated three times to yield white polymers after freeze-drying of the soluble form.

b) Ultrafiltration by using a specific membrane of 3.000 Mw was also tested, leading to the purified compounds after freeze-drying of the samples.

c) Sephadex G25 (Size Exclusion Chromatography (SEC)) columns were also tested for the purification of the compound leading to a good separation by Mw of the corresponding polymer. The compound was obtained purified in the first fractions after freeze-drying of the sample.

In all the cases the product was obtained pure and with comparable yields (~80%). It has to be said that ultrafiltration is preferable when large amounts of compound are prepared and Sephadex G25 (PD10) columns are preferred when little amounts of compound are prepared. In between, the three methods are completely valid for the purification of the polymeric compound. Once purified the alkyne content was quantified by integration of the corresponding signals of the alkyne in the registered $^1$H-NMR spectra in deutered water, in comparison with the corresponding signals of PGA. Concretely, the pick situated at 3.81 ppm corresponds with the two protons of the CH$_2$ of the propargyl residue, and the signal at 2.48 ppm corresponds with the acetylenic proton of the propargyl residue. Thus, in comparison with the protons of PGA, the % of substitution of each polymer was calculated. Different polymers with different degree of substitution were synthesized. The degree of substitution according to H-NMR was approximately 60% of what it was expected from the equivalents added. The results are summarized in the table below.

TABLE 9

Modified polymers with alkyne groups

| Polymer | | Alkyne Content (calc.) (%) | Alkyne Content ($^1$H-RMN) (%) | Mn | Mw | PDI |
|---|---|---|---|---|---|---|
| 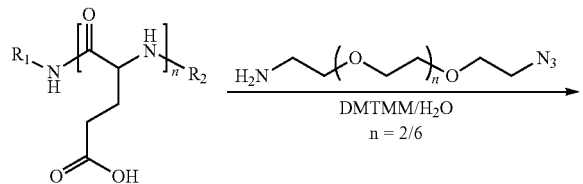 | 46 | 50 | 31 | 19250 | 25020 | 1.3 |
| | 47 | 30 | 18 | 18590 | 24170 | 1.3 |
| | 48 | 20 | 11 | 18230 | 23700 | 1.3 |
| | 49 | 10 | 6 | 17980 | 23370 | 1.3 |

The resulting Mw of the polymer was calculated taking into account the % of modified units of glutamic acid (GA). As an example:

Post-Polymerization Modification with $NH_2$-PEG(2)-$N_3$ and $NH_2$-PEG(6)-$N_3$.

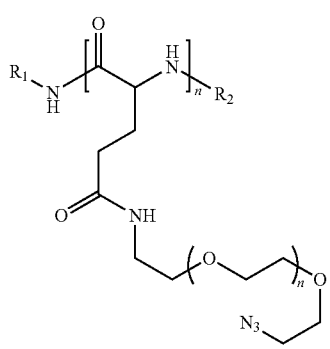

wherein, n represents number of glutamic units, from 1 to 1000 x represents number of units of glutamic modified with ethilenglycol, from 1 to 1000

The same procedure used for the incorporation of oligoethylenglicol azides into the polymer backbone. Once purified the oligoethylengNcol content was quantified by integration of the corresponding signals of the ethylenglicol unit in the registered $^1$H-NMR spectra in deutered water, in comparison with the corresponding signals of PGA. Concretely, the picks at 3.26, 3.35 and 3.48 ppm correspond with the $CH_2$ protons near to the amide group and the azide group. The big signal at 3.55 ppm does correspond with the $CH_2$ located inside the oligoethylenglycol chain plus one of the triplet corresponding to the exterior $CH_2$ protons. This latter signal changes in its integration whenever the modification is done with $EG_2$ (two units of ethylenglicol in the inside chain which correspond with 10 protons) or $EG_6$ (which corresponds with 50 protons). Thus, in comparison with the protons of PGA, the % of substitution of each polymer was calculated Once more, different polymers with different degrees of substitution were synthesised. The degree of substitution according to $^1$H-NMR was approximately 70-80% of the theoretical value for low substitution and around 60% for higher substitutions. The results are summarised in the table below.

TABLE 10

OligoEG azide modified polyglutamates

| Polymer | | Azide Content (calc.) | Azide Content ($^1$H-RMN) | Mn | Mw | PDI |
|---|---|---|---|---|---|---|
| 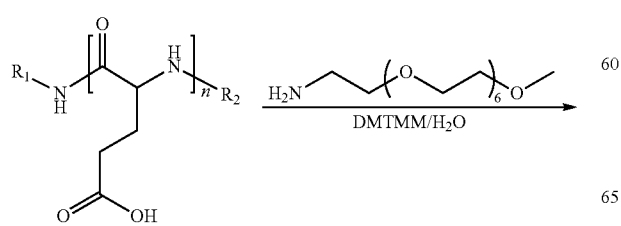 | 50 | 15 | 11 | 23500 | 30500 | 1.3 |
| | 51 | 20 | 16 | 24700 | 32100 | 1.3 |
| | 52 | 60 | 30 | 22500 | 29200 | 1.3 |
| 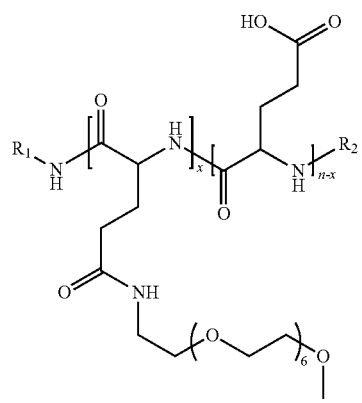 | 53 | 20 | 16 | 26000 | 33800 | 1.3 |
| | 54 | 30 | 18 | 26500 | 34400 | 1.3 |
| | 55 | 50 | 34 | 27200 | 35400 | 1.3 |

The Mw of the resulting copolymers was calculated taking into account the Mw of the oligoethylenglicol units in each case PEGylation of PGA.

Different polymers with different degree of pegylation within the polymer backbone were synthesized in order to study the different physic-chemical properties that the PEGylation could provide to the polyglutamic acid architectures. For that purpose a metoxy-oligoethylenglycol-amine was used following the same protocol as described before. The set of polymers is summarized in the table below.

wherein,
n represents number of glutamic units, from 1 to 1000
x represents number of glutamic units modified with ethylenglicol, from 1 to 1000

TABLE 11

Metoxy-oligoEG modified polyglutamates

| Polymer | | Oligo EG content (%) (calc.) | Oligo EG content(¹H-RMN) (%) | Mn | Mw | PDI |
|---|---|---|---|---|---|---|
| 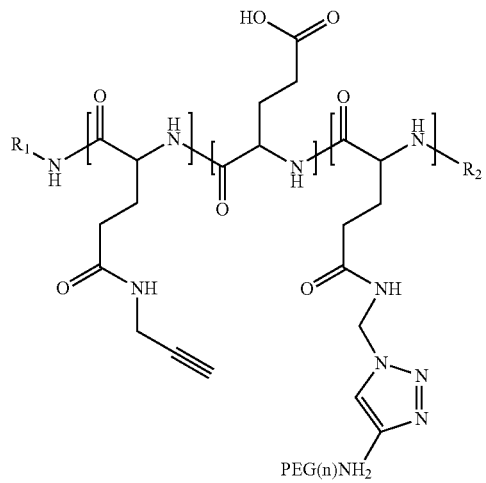 | 56 | 200 | 87 | 56000 | 72700 | 1.3 |
| | 57 | 140 | 73 | 49800 | 64700 | 1.3 |
| | 58 | 100 | 49 | 39200 | 51000 | 1.3 |
| | 59 | 60 | 30 | 30900 | 40200 | 1.3 |
| | 60 | 20 | 8 | 21200 | 27600 | 1.3 |
| | 61 | 75 | 50 | 21200 | 25000 | 1.18 |
| | 62 | 50 | 33 | 17400 | 22600 | 1.18 |
| | 63 | 25 | 24 | 15600 | 1840 | 1.18 |

Post-Polymerization Modification by Click Chemistry.

Click Chemistry Model Couplings

In a two bottle-neck round bottom flask fitted with a stirrer bar and a stopper, 1 eq of copolymer (PGA and EG(2)N, EG(6)N₃ or propagylamine in each case) sodium salt was dissolved in milliQ water. After that, the corresponding amount for the desired % of substitution of clickable agent was added in dry DMF solution. Then, five equivalents of Sodium ascorbate in milliQ water solution were added (Mw=198.11 g/mol). After that, the mixture was degassed by performing two freeze-pump-thaw cycles. Afterwards, one equivalente of $CuSO_4$ (Mw: 249.68 g/mol) was weighted under $N_2$ flow and added in $H_2O$ milliQ solution to the reaction mixture. The final complete mixture, containing a proportion $DMF/H_2O$ of 4:1, was degassed by performing another freeze-pump-thaw cycle and left to react at 40° C. in an oil bath from 3 days protected from the light.

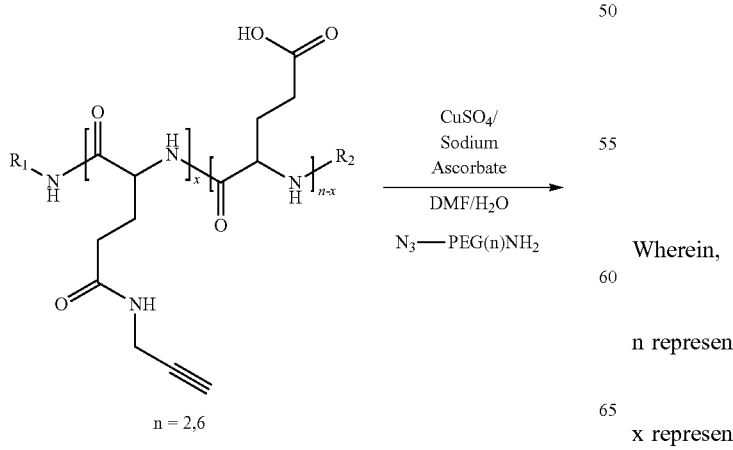

-continued

Wherein, n represents number of glutamic units, from 1 to 1000 x represents number of glutamic units modified with ethylenglycol, from 1 to 1000

TABLE 12

Model click chemistry reactions conditions and results between PGA modified with alkyne groups and oligoEG-azides

| Experiment | Solvent | T° °C. | Catalyst System | Eq. per unit | Linking Efficacy |
|---|---|---|---|---|---|
| [PGA-alkyne structure] + N₃-(CH₂CH₂O)₂-CH₂CH₂-NH₂ | H₂O | 40 | CuSO₄/NaAscorbate (0.3/0.5) | 3 (20%) | 88% |
| | H₂O | 40 | CuSO₄/NaAscorbate (1/5) | 6 (40%) | 97% |
| | DMF/H₂O | 40 | CuSO₄/NaAscorbate (0.3/0.5) | 6 (40%) | 48% |
| | DMF/H₂O | 40 | CuSO₄/NaAscorbate (1/5) | 2 (9%) | 67% |
| N₃-(CH₂CH₂O)₆-CH₂CH₂-NH₂ | H₂O | 40 | CuSO₄/NaAscorbate (1/5) | 6 (40%) | 96% |

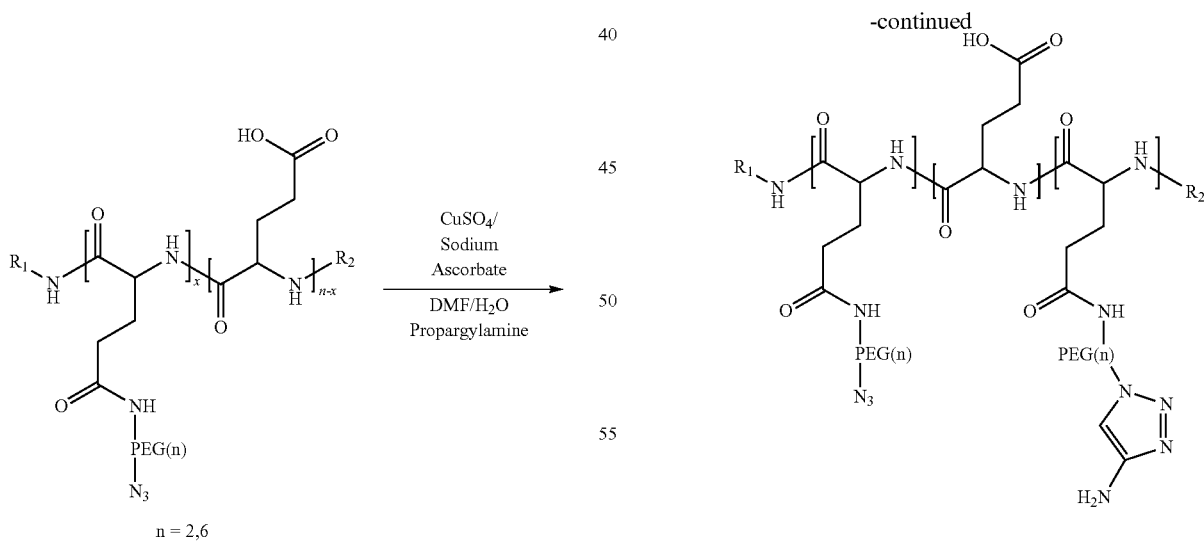

Wherein, n represents number of glutamic units, from 1 to 1000 x represents number of glutamic units modified with propargylamine, from 1 to 1000

TABLE 12

Model click chemistry reactions conditions and results between PGA modified with alkyne groups and oligoEG-azides

| Experiment | Solvent | T° °C. | Catalyst System | Eq. per unit | Linking Efficacy |
|---|---|---|---|---|---|
| | $H_2O$ | 40 | $CuSO_4$/ NaAscorbate (0.3/0.5) | 3 (20%) | 88% |
| | $H_2O$ | 40 | $CuSO_4$/ NaAscorbate (1/5) | 6 (40%) | 97% |
| | DMF/ $H_2O$ | 40 | $CuSO_4$/ NaAscorbate (0.3/0.5) | 6 (40%) | 48% |
| | DMF/ $H_2O$ | 40 | $CuSO_4$/ NaAscorbate (1/5) | 2 (9%) | 67% |
| | $H_2O$ | 40 | $CuSO_4$/ NaAscorbate (1/5) | 6 (40%) | 96% |

From the results obtained, the following conclusions can be drawn:

The optimal conditions in aqueous solutions are: the use of $CuSO_4$/NaAscorbate (1/5) as catalyst system at 40° C. leading to a linking efficiency of 96-97%.

The use of CuBr/PMDTA (1:1) in DMF mixtures does not work either at room temperature or 40° C. Probably an additional use of sodium ascorbate to prevent the oxidation of Cu(I) could be determined as the solution. By the way, the use of DMF/$H_2O$ mixtures (4:1) with $CuSO_4$/NaAscorbate (1/5) also allows the possibility of the conjugation of hydrophobic peptides/drugs. The linking efficiency is always less when DMF/$H_2O$ mixtures are used, but acceptable and more or less predictable.

Post-Polymerization Modification Through Amide Bonds DTPA/DOTA Conjugation

Gadolinium/galium complexes like Gd-DTPA, Ga-DOTA or their derivatives are usually exploited as magnetic resonance imaging (MRI) contrast agents and Positron Emission Tomography (PET), respectively. The percentage of Gd or Ga introduced directly depends on the number of glutamic units of the peptide block. Aiming at complexing Gd and Ga complexing units, such as, DTPA-dianhydride (diethylen-etriaminepenta-acetic acid dianhydride) or DOTA (1,4,7,10-tetraazacyclododecane-1,4,7,10-tetraacetic acid) are required. Carboxylic groups of PGA are functionalized with a monoprotected diamine, with the objective of having a free $NH_2$ (after deprotection) which will react with DTPA-dianhydride or DOTA through an amide bound. Monoprotected diamine avoids crosslinking processes.

Taking into account that the number of carboxylic groups can be varied, percentage of complexed Gd or Ga can be customized. The coupling of the diamine to the carboxylic groups of the tri-block, followed by coupling of the chelanting agent DTPA/DOTA for final complexation to Gd/Ga, was performed following the protocol described bellow, obtaining variable diamine loading.

First of all, as the TB is obtained in its sodium salt form it has to be acidified to become soluble in DMF. Acidification is carried out by dissolving the polymer in the minimum volume of water and HCl 6N is dropwise added while pH is controlled. At pH around 4, precipitation is observed. After centrifugation, pellet and supernatant are freeze-dried. Detailed analysis of conjugation is exposed bellow.

1) 2.2Fmoc(aminoethoxy)ethylamine
2) DMF/piperidine) 4:1
3) DTPA

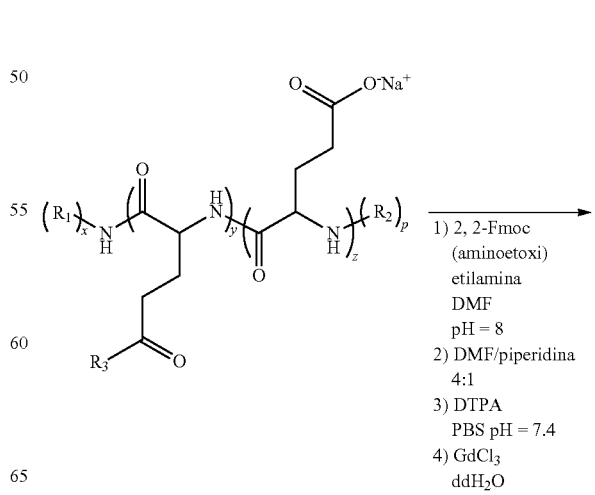

-continued

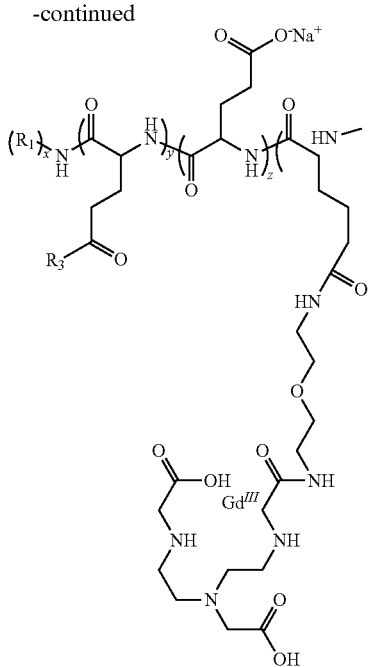

wherein:
R1 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol).

R2 represents an alkyl group with Defined C-terminal attachment group (alkyne, azyde, thiols, halides, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol), PEG-thiol, PEG-4TP.

R3 represents an alkyl group with Defined C-terminal attachment group (alkyne, azyde, thiols, halides, activated thiols, alkenes, activated esters, activated alcohols, protected amines, maleimide groups, acetals, activated carboxylic acids), ethylenglicol (EG) of different molecular weights including polyethylenglicol (PEG, from n=2 to n=16); amino acids such as lysine, arginine, imidazole, histidine and cysteine, and secondary and tertiary amino groups.

x represents number of monomer units into definition R1, from 1 to 500 y represents number of glutamic units modified with R3 in the polymer, from 1 to 500 z represents number of glutamic units not modified in the polymer, from 1 to 1000 p represents number of monomer units included into R3 definition, from 1 to 500

TB200 (34.5 mg; 31044 g/ml, 1.11 $10^6$ mol) is dissolved in 5 ml of anhydrous DMF, at RT under $N_2$. After dissolution, 1.5 (per 200 residues of GA) eq of DIC were added and, after 5 min, 1.5 (per 200 residues of GA) eq of HOBT. After 10 min stirring, the protected Fmoc-diamine was added in the reaction (59 mg; 362.85 g/ml; 1.62 $10^{-4}$ mol; 200 eq). The pH was adjusted to 8 with 300 μl of DIEA and the reaction carried out for 24 h and followed by TLC. DMF was evaporated under vacuum and non-reacted Fmoc-diamine was removed washing with 8-10 mL $CHCl_3$:acetone (4:1) and non-reacted Fmoc-diamine present in the organic solvents was quantified with absorbance analysis at 290 nm. The net step is to deprotect the Fmoc-diamine linked to the polymer. Deprotection was performed with DMF:piperidine (4:1) at RT, under $N_2$ for 1 h. The free Fmoc are removed again by washing the product in $CHCl_3$: acetone (4:1). Then, the supernatant was dried and resuspended in MeOH for analysis at 290 nm (in order to quantify the Fmoc groups) while the pellet was dried under $N_2$ for following reaction steps. With the spectrophotometric analysis, percentage of diamine coupling was checked[1].

[1] Absorbance assays have varied every time that this synthesis has been carried out.

$Gd^{3+}$ Chelation

For $Gd^{3+}$ chelation, the ratio 1 eq DTPA:1 eq $GdCl_3$ was considered, and a DTPA conjugation efficiency of 50% was supposed. The freeze-dried TB was resuspended in an appropriate volume of water (in order to achieve a final concentration of PBS 1×), while $GdCl_3$ (263.61 g/mol, 1.14 $10^4$ mol) in water (concentration=100 mg/ml solution) was added dropwise to the aqueous solution of TB-DTPA. During this step, the pH must be monitored and constantly adjusted to 8 adding NaOH.

The presence of trace amounts of non-chelated $Gd^{3+}$ ions in the mixture was monitored with a $Gd^{3+}$ indicator, 4-(2-pyridylazo)resorcinol, that change colour from yellow to orange in presence of non-chelated $Gd^{3+}$.

After 4.5 h of reaction, no free $Gd^{3+}$ was detected and the reaction stopped by freeze-drying the water. The product was further purified by gel filtration on a PD-10 column for desalting. It is planned to determine $Gd^{3*}$ amount in the compound by atomic absorption. Yield=50%

The same procedure, with appropriate quantities, was carried out also with a sample of TB800 in order to have the possibility of enhancing $Gd^{3+}$ amount into the carrier.

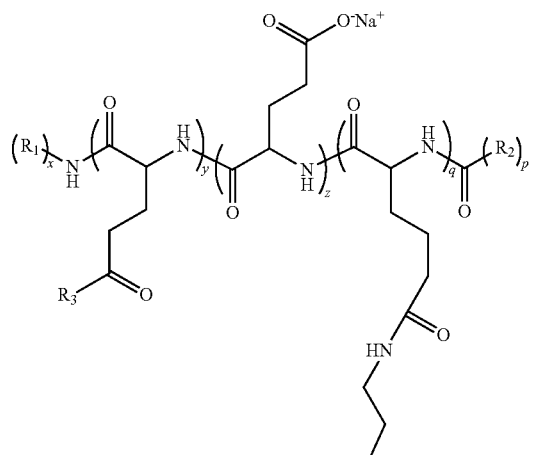

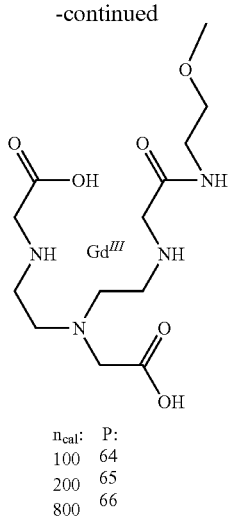

$n_{cal}$: P:
100   64
200   65
800   66

Wherein,
x represents number of monomer unit included into R1 definition, from 1 to 500
y represents number glutamic units modified with group R3 in the polymer, from 1 to 1000

| Product | | % free Fmoc-diamine | % Fmoc (=diamine grafted) |
|---|---|---|---|
| GI-21 | TB200 | 138% | 6% |
| GI-24 | TB200 | 70% | 30% |
| GI-40 | TB800 | 107% | 8% |
| GI-40bis | Tb800 | 71% | 30% | z represents number glutamic units without modification in the polymer, from 1 to 1000
q represents number glutamic units modified with DTPA in the polymer, from 1 to 1000
p represents number of monomer units included into R2 definition, from 1 to 500
$n_{cal}$ represents number of theoretical monomer units in the polymer, from 1 to 1000
In the case DOTA-Ga, after obtaining the soluble form of the polyglutamate in DMF (previously precipitated by acid-base addition up to pH=4), conjugation is performed to obtain the following PGA-DOTA family of derivates that are detailed bellow.

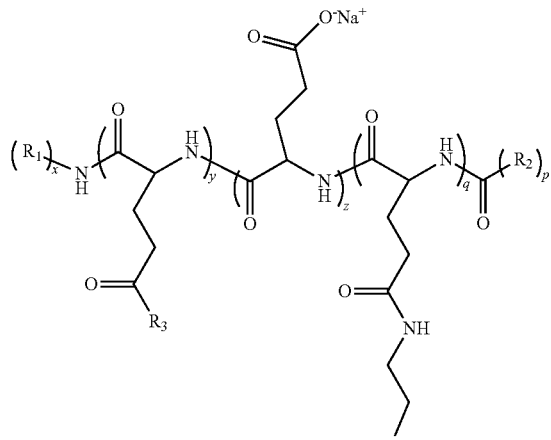

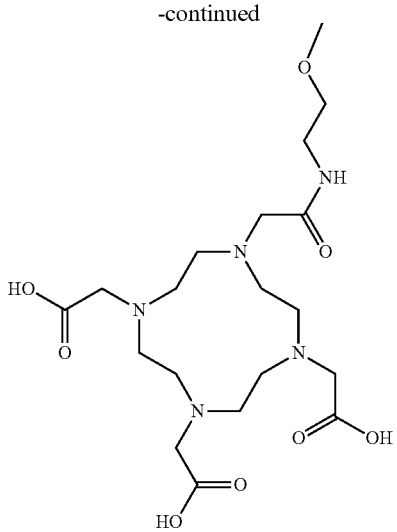

wherein:
R1 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol).
R2 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from 100 to 20000 g/mol), PEG-thiol, PEG-4TP.
R3 represents an alkyl group with Defined C-terminal attachment group (alkyne, azyde, thiols, halydes, activated thiols, alkenes, activated esters, activated alcohols, protected amines, maleimide groups, acetals, activated carboxylic acids), ethylenglicol (EG) of different molecular weights including polyethylenglicol (PEG, from $n=2$ to $n=16$); amino acids such as lysine, arginine, imidazole, histidine and cysteine, and secondary and tertiary amino groups.
x represents number of monomer units into definition R1, from 1 to 500
y represents number of glutamic units modified with R3 in the polymer, from 1 to 500
z represents number of glutamic units not modified in the polymer, from 1 to 1000
p represents number of monomer units included into R3 definition, from 1 to 500
In a round bottom flask, PGA (1 eq, average MW GA unit=129 g/mol) was placed and system was purged under constant nitrogen flow. Product was dissolved with 20 mL of anh. DMF. Then, 1.5 eq of DIC (0.35 mmol, 0.836 g/cm³, 126.20 g/mol) was added to the reaction and after 5 min, 1.5 eq of HOBt (0.35 mmol, 135.10 g/mol) was incorporated as a solid. 10 min later, DOTA-NH$_2$ derivate (tert-butyl 2,2', 2"-(10-(2-(2aminoethylamino)-2oxoethyl)-1,4,7-tetrazacyclododecane-1,4,7-triacetate)eq. depending on the derivatization required 0.02-0.1 eq. 614.82/mol) dissolved in anhydrous DMF was added dropwise to the reaction containing activated polymer. pH adjusted to 8 with DIEA. After 48 h stirring at RT, solution was concentrated under high vacuum. Purification was performed by precipitation of the concentrated solution in an excess of cold acetone. Pale yellow precipitate was recovered after centrifugation (2600 rpm, 4° C., 10 min) and dried under vacuum. Percentage of DOTA conjugation was calculated by 1H-NMR analysis (D2O) (between 2-10 mol %).

Alternatively, in a round bottom flask, DB200 (0.7166 mmol, 1 eq, average MW GA unit (salt form)=171.31 g/mol) were dissolved in 5 mL of ddH$_2$O. DMTMM-CI (0.0717 mmol, 0.115 eq, 0.836 g/cm$^3$, 126.20 g/mol) was added to the reaction and after 10 min, DOTA-NH$_2$ (for 11.5% mol, 0.0717 mmol, 0.115 eq, 614.82/mol) previously dissolved in anhydrous DMF (1 ml) was added dropwise to the reaction. pH adjusted to 8 with DIEA. After 48 h stirring at RT, solution was concentrated under high vacuum. Purification was performed by precipitation of the concentrated solution in an excess of cold acetone. A pale yellow precipitate was recovered after centrifugation (2600 rpm, 4° C., 10 min) and dried under vacuum. Percentage of DOTA conjugation was calculated by 1H-NMR analysis (D$_2$O) (between 2-12 mol %). Reaction yields >70%.

To avoid crosslinking reactions, carboxyl groups are normally protected, for example ter-butyl. Theses carboxyl are deprotected before complexing of $^{68}$Ga in a CH$_2$Cl$_2$/TFA (3:2, v/v) mixture stirred for 15 at room temperature, or in a mixture of TFA/H$_2$O/TIS (95:2.5:2.5 v/v) for 3 hours at room temperature. Conjugate can then be isolated through precipitation in an excess of cold dietilic eter, then washed and dried under vacuum. Quantitative Yield. Complete depretection ratified by, 1H-NMR Toxicity and Cell Viability Assay Through the MTT Assay The MTT assay measures cell proliferation as well as reduction in cell viability when metabolic events lead to apoptosis or necrosis. It can also be used to assess the rate of survival of a given cell line when it is incubated in the presence of xenobiotics. The reduction of tetrazolium salts is accepted as a reliable way to analyze cell proliferation. The yellow tetrazolium MTT (3-(4,5-dimethylthiazolyl-2)-2,5-diphenyltetrazolium bromide) is reduced by metabolically active cells and results in the intracellular formation of purple formazan that can be spectrophotometrically measured after solubilization with DMSO.

The MTT assay was used in this invention to assess the toxicity of compounds at different concentrations. To analyze their potential impairment in cell viability, compounds were added to HeLa and HUVEC cell lines at different concentrations and incubated up to 72 h.

Results are shown in FIGS. 9A and 9B where it can be observed that for the compounds TB400 [P: 35 wherein X=OMe or S-S-4TP] and TB800 [P: 36 wherein X=OMe or S-S-4TP] cell viability is over 80% following 24 or 72 hours of incubation with HUVEC cells. FIG. 9B shows a comparation study where cell viability of the compound TB200 [P: 34 wherein X=OMe or S-S-4TP] is measured in different cell lines (HUVEC and HeLa) at various incubation times.

Cellular Internalization Studies

Synthesized polymers have been studied comparing different molecular weights and conformation in. Hela and HUVEC cells. Flow cytometry (FIG. 2A) and live-cell confocal fluorescence microscopy (FIG. 2Ab) have been used with polymers labelled with Oregon green (OG-Cadaverine). Synthesized polymer with —COOH deprotected groups (P—COOH, 1 equiv.) are dissolved in anhydrous DMF under N$_2$ atmosphere, subsequently the dye (OG-NH$_2$ 0.1 equiv.) is added in anhydrous DMF together with triethylamine (up to pH=8). The reaction is monitored by TLC, and once terminated the polymer is purified by SEC (PD10 columns, Sephadex) and the fluorescent loading is determined with the fluorimeter (fluorescence quantification of crude and purified polymer). TB10 was found out of the detection limit of the system, therefore TB-OG50, TB-OG100 and TB-OG200 were analyzed. Internalization studies were carried out in the presence of leupeptine (thiol protease inhibitor) to avoid degradation of the polymer carrier.

In Hela cells, whilst TB50 and TB100 showed a lineal increase in the associated cell fluorescence, TB200 shows a quicker internalization reaching stability before 5 hours. On top of this, at 4° C., TB200 presents and increased associated fluorescence at early timepoints, more precisely at 30 minutes pointing out the possible presence of combination of cellular internalization mechanisms (according to energy-dependent (i.e. endocytosis)+independent mechanisms (i.e. diffusion)). This observation is confirmed by the graphs and confocal microscopy images shown in FIGS. 10A and 10B.

This mixed internalization mechanism is not observed in HUVEC cells for any of the analyzed polymers (FIGS. 11A and 11B). HUVEC cells internalize TB through endocytosis (lysosomal colocalization FIG. 11B) and internalization capacity is also much higher that the observed for HeLa cells for the same compounds (compare FIGS. 10A and 11A). All assays were performed using the same OG equivalents. Images obtained with lipidic membrane marker also demonstrate that polymers do not associate to plasma membrane and are almost quantitatively internalized (FIG. 10B).

Degradation Studies in a Buffer at Different pH Values, in Plasma and in Presence of Catepsin B.

To study hydrolitic and enzymatic biodegradability of the new synthesized polymers different stability studies were performed as detailed bellow. AI of the samples taken were analysed by HPLC and GPC Degradation at Different pH Polymers were dissolved in PBS buffer pH 5.5, 6.5 and 7.5 at a concentration of 3 mg/mL. Solutions were incubated at 37° C., and 100 □L samples were taken at different times, then frozen for its future analysis.

Plasma Degradation

To obtain blood plasma, fresh blood from rat/mouse was centrifuged at 12000 rpm during 10 minutes at 4° C. Supernatant (plasma) was separated from pellet (cells) and used to dissolve polymers at a final concentration of 3 mg/mL. Solutions were incubated at 37° C. and 100 □L samples were taken at different times, then frozen for its future analysis.

Enzymatic Degradation (Catepsin B)

Polymers were dissolved in sodium acetate buffer 20 mM pH 6.0 at a concentration of 3 mg/mL in the presence of EDTA 2 mM, DTT 5 mM and 6.25 units of catepsin B (dissolved in acetate buffer). Solutions were incubated at 37° C. and 100 □L samples were taken at different times, then frozen for its future analysis.

Biodistribution Studies

Animal studies were performed according to local legislation and only after approval of the Ethical Comitee of Animal wellbeing of CIPF, and according to the European legislation in place. Animals were kept respecting their wake-sleep cycles of 12 h and controlling temperature and humidity environment conditions, food and water was also provided.

Biodistribution Studies with Fluorescence Labelling. Using Oregon Green (OG) as a Probe.

Oregon Green In Vivo Studies

For biodistribution investigation, ex vivo studies are being carried out analysing accumulation of fluorescent tri-block in different rat organs by HPLC and spectrofluorometer device. A rat was injected with 14 mg/ml of TB200 labelled with Oregon Green and sacrificed after 4 h (experiment called TBO-4 h); a second rat was injected with the same quantity but sacrificed after 24 h (experiment TBO-24 h). As a control experiment, a rat was injected with 14 mg/ml of TB200 not labelled and it was sacrificed after 4 h (experiment TB-4h).

Immediately after scarification, the blood was collected and organs removed, weighted, frozen in liquid nitrogen and stored at −80° C. for following analysis. The tissues under investigation are brain, cerebellum, hearth, spleen, liver, bladder, stomach, gut, muscle and fat. Each organ was treated with a solution of $HClO_4$ 6%/EtOH 40% (4 ml per each gram of tissue) and homogenized. Also serum was treated with the same protocol: blood vials were centrifuged in order to remove serum (supernatant); the same volume collected was added of the perchloric acid solution. The suspension was centrifuged for 60 min at 4000 g at 4° C., the supernatant stored for analysis and the pellet freeze-dried.

In order to improve the extraction of the polymer, pellets were sonicated for 1 h in 1 ml of $NaHCO_3$ 1M/2 ml of $H_2O$, centrifuged at the same condition and the supernatant stored for further analysis.

As it was found that Oregon Green is pH sensitive (the fluorescence is inhibited acidic pH), the $HClO_4$ supernatant were neutralized with NaOH, freeze dried and resuspended in 1 ml of PBS at pH 8 for further analysis.

The serum of the animals was separated from the collected blood by centrifugation and mixed to an equal volume of $HClO_4$ 6%/EtOH 40%.

All the samples ($HClO_4$ supernatant, basified supernatant, $NaHCO_3$ supernatant) have been analysed (or are ongoing) both with a spectrofluorometer and with HPLC. Some preliminary results are summarized below. Conclusions should be analyzed deeply together with the HPLC fluorescence chromatograms (data not shown).

Serum fluorescence was checked in the spectrofluorometer directly(blue bar), after supernatant after $HClO_4$ solution addition (violet), after washing with MeOH the pellet of the latest treatment (yellow) and after ACN washed of the pellet (light blue. It is observed that serum fluorescence is lost after $HClO_4$ treatment. This conclusion makes possible that the TBO precipitates with the other proteins (maybe is forming aggregates with the plasmatic proteins). Due to this fact, $NaHCO_3$ washed of the pellet has been performed in the tissues, in order to obtain the sodium salt of the tri-block and solubilise it to the aqueous phase for its subsequent fluorescence measuring.

The serum followed a similar treatment: after blood centrifugation, the supernactant was collected and same volume of the perchloric acid solution added dropwise. After sample centrifugation (10 min, 12000 rpm, 40) the supernactant was collected for further analysis.

For biodistribution studies in vivo of the homopolypetides di- and tri-blocks the different organs (Wistar rats) were analysed by High Pressured Liquid Chromatography (HPLC) and fluorimetry. As a preliminary example of the present invention, the experiment that took place with TB200 labelled with OG is detailed bellow.

Rat intravenous injection of 14 mg/mL TB200 labelled with OG. Rat was sacrified 4 h after injection (experiment name TBO-4h); a second rat was injected following the same procedure and sacrified 24 h later (TBO-24H). As a control, a rat was intravenously injected with 14 mg/mL of TB200 without labelled and sacrified 4 hours later (TB-4H).

Immediately after sacrifice, blood was collected, organs were weight and frozen in liquid nitrogen and stored at −80° C. Analyzed organs included brain, cerebellum, heart, liver, kidney, bladder, stomach, intestine and muscle. Each of them treated with a lysis solution consistent on 40% EtOH/6% $HClO_4$ (4 mL per tissue gram). Sample was homogenated with Ultraturrax (aprox. 1 min, 13000 rpm). Suspension was centrifuged for 60 min at 4000 g and 4° C., and supernatant was collected for analysis. Serum followed a similar procedure; after blood centrifugation, supernatant was collected and an equal dissolution volume was added of perchloric acid. After centrifugation of the sample (10 min, 12000 rpm, 4° C.), supernactant was collected for analysis.

To increase the extraction of the polymer from the mixture, the obtained pellets underwent ultrasound for 1 h after adding 2 mL dd$H_2O$ and 1 mL of a 1M $NaHCO_3$ solution. After centrifugation samples with the previously mentioned conditions and the supernactant was kept for analysis.

After observing that the sensibility of OG at the pH of the solution (fluorescence decreases considerably at acid pH), after treatment with perchloric acid supernactants were treated with NaOH, liophilised and redissolved in 1 mL PBS pH=8 for future analysis.

All samples, tissues and serums, (supernactants of the treatments with the perchloric mixtures, basified supernatants of perchloric mixtures and supernactants of the treatment with $CO_3HNa$ were studied by HPLC and fluorescent espectrophotometer. Preliminary results of the analysis are shown in FIGS. 12A and 12B.

Plasma fluorescence (FIG. 12A) was quantified with a spectrofluorometer: directly after treatment with perchloric mixture, after washing with methanol of the pellet obtained in the previous treatment and after the wash with acetronile of the same pellet. In the graphs shown in FIG. 12 we can observe that the starting fluorescence seen in plasma was gradually lost after treatment with perchloric mixture. In spite of this conclusion the possibility of finding precipitates of TBO together with other proteins present in the plasma exists (it could be that this polymeric specie could form aggregates with other plasmatic proteins). As a consequence, pellet was washed with a solution of sodium bicarbonate as previously described for tissues, with the aim of obtaining sodium salts of the triblock and solubilize it in the aqueous phases for its subsequent analysis through fluorescent measurements.

Biodistribution Studies with Fluorescent Labelling. Use of Cyane5.5 (Cy5.5) as a Probe.

In a parallel study to the previously described, polymer labelling took place using a fluorescence probe with near infrared emission and high penetrability in tissue, Cyane5.5 (Cy5.5, λexc. 675 nm, λem 694 nm). The in vivo study took place in mice without thymus nude Fox1n nu/nu. Following intravenous injection of polymeric compounds labeled with Cy5.5, fluorescence images were taken in vivo and subsequently ex vivo (of extracted organs) by using the optical imaging platform Xenogen IVIS) Spectrum. This system allows visualization, follow-up and quantification of genetic and cellular activities inside a living organism at real time, through bioluminescence or fluorescence, as well as ex vivo organs and in vitro assays.

In this study we used the methodology described before for the labelling with OG. As a preliminary example of the present invention, an assay with DB100 labelled with Cy5.5 that was performed is described in detail bellow. The sole exception is that the sensibility of Cy5.5 to pH was not the same than in OG, and therefore washing of the pellets with NaHCO$_3$ 1M was not necessary as they did not supply additional information. An example of the images obtained is shown in FIG. 13.

Biodistribution Studies by Magnetic Resonance Imaging (MRI)

Imaging through magnetic resonance is a non-invasive non-ionizing technique that uses the phenomenon of magnetic resonance to obtain Information regarding structure and composition of the subject analyzed. It's a unique tool for contrast amongst tissues, and is able to distinguish between sane and unhealthy tissues.

The use of contrast agents in MRI is justified when it is not possible to modify the inherent tissue contrast to obtain a higher resolution of images. These agents are based in the changes in the longitudinal (T1) and transversal (T2) relaxing times of the water protons and/or in the magnetic susceptibility of water in the tissues where it accumulates. An MRI contrast agent is divided into two components: metallic ion with magnetic properties, free form is toxic for the organism, and a chelate that on top of preventing toxicity of the free ion, allows adjustment pharmacokinetics of the product according to interests.

In the present invention gadolinium metal (Gd) has been used as a contrast agent due to its paramagnetic properties, which increase relaxing time of T1 protons of the water.

For in vivo MRI, the hydrogen nuclei has been selected as the best target as it is the one to produce the highest MRI signal relative to all the nuclei present in all the tissues, and the best contrast amongst the tissues as it provides several ways to manipulate contrast in final image.

Preliminary studies in vivo using this technology were performed to determine the biodistribution of the new polymers through an alternative methodology than that provided by fluourescence described in this document, as well as to compare which of them provides the best characteristics for its future conjugation to the drug. TB200-DTPA and TB800-DTPA triblocks labelled with Gd were intravenously injected into rats, at a dose of 0.2 mmol Gd$^{3+}$ per kg of animal and monitored by MRI. The experiments were performed in a Bruker Pharmascan (Bruker Medical Gmbh R, Ettlingen, Germany) system. The contrast agent was administered through the tail vein as a bolus 9 minutes after starting of the adquisitlon.

Figure 14:
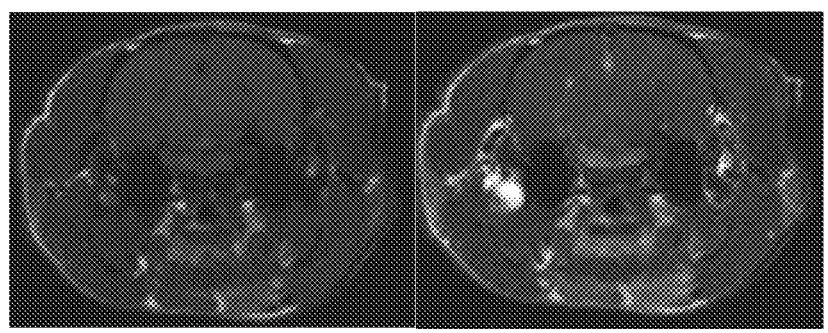

Results of the experiments previously described allowed detection of the conjugates in circulation without observing specific accumulation in any tissue, as for example brain (see FIG. 14). No toxicity effects were observed. Both products did not result toxic in the animals demonstrating biocompatibility.

Biodistribution Studies by Positron Emission Tomography (PET)

Positron Emission Tomography (PET) is a technique used to quantitatively determine the in vivo concentration of positron emiting labelled compounds. The quantity measured by PET corresponds to in vivo regional concentration of emiting positrons that can also allow metabolic study.

In the present invention Galium metal was used ($^{68}$Ga) as a radioisotope due to its half-life (68 min) and its complexation requirements (DOTA). This radiotracer has been also described as the best candidate for neuroendocrine tumors due to somatostatine recognition. Monitoring has taken place in a PET-CT. PET-CT equipment offer the advantage of using direct anatomical correlation in case of unprecise diagnostic.

Figure 15:
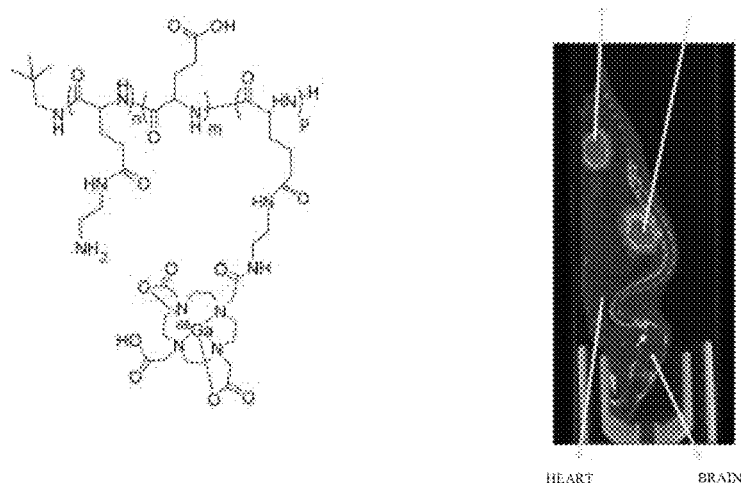
Figure 15:
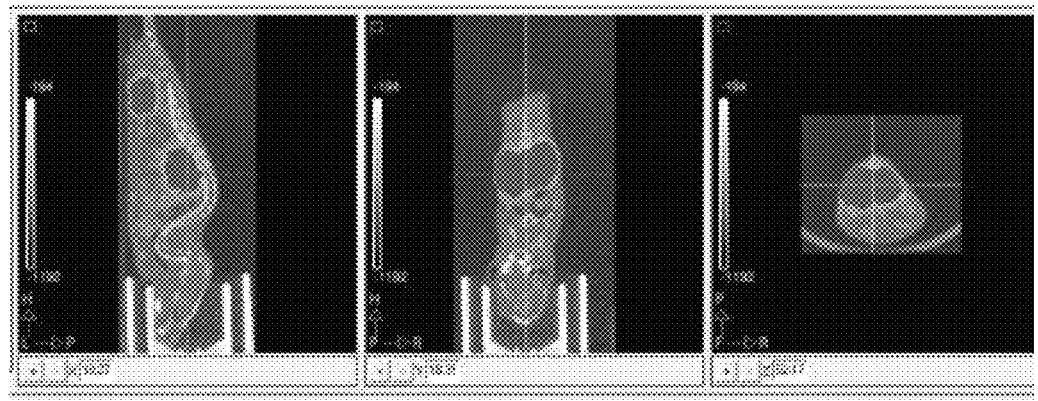

Preliminary studies of biodistribution by PET have been performed (FIG. 15). These studies have allowed us to detect the presence of conjugates in circulation without observing accumulation in specific tissues, as for example in brain, liver, lungs and a clear renal release (see FIG. 15). No toxicity effects have been described in the cases studied.

REFERENCES

1. Gaspar R., Duncan R (2009) Polymeric carriers: preclinical safety and the regulatory implications for design and development of Polymer Therapeutics, Adv. Drug Dellv. Rev., 61, 13, 1220-1231
2. Barz M, Luxenhofer R, Zentel R, Vicent M J. Defined polymers for therapeutic applications: From Structure-Property Relationships to better defined Therapeutics. Polymer Chemistry, DOI: 10.1039/c0py00406e
3. Deming, T. (2002) Methodologies for preparation of synthetic block copolypeptides: materials with future promise in drug delivery Adv. Drug Delivery Rev. 54; 1145.
4. Wang, X. Y.; Kim, H. J.; Wong, C.; Vepari, C.; Matsumoto, A.; Kaplan, D. L. (2006) Fibrous Proteins—Role in Biomaterials and Tissue Engineering. Mater. Today 9: 44-53.
5. Dos Santos, S.; Chandravarkar, A.; Mandal, B.; Mimna, R.; Murat, K.; Saucede, L.; Tella, P.; Tuchscherer, G.; Mutter, M. J. Am. Chem. Soc. (2005)127: 11888-11889.
6. Mart, R. J.; Osborne, R. D.; Stevens, M. M.; Ulijn, R. V. (2006) Peptide-based stimuli-responsive biomaterials Soft Matter 2: 822-835.
7. Li C., Wallace S., Polymer-drug conjugates: recent development in clinical oncology, Adv. Drug. Deliv. Rev. 60 (2008) 886-898
8. Singer, J. W., Shaffer, S., Baker, B., Bemareggi, A., Stromatt, S., Nienstedt, D., Besman, M. (2005) Paclitaxel poliglumex (XYOTAX; CT-2103): an intracellularly targeted taxane. Anticancer Drugs, 16(3), 243-254.
9. Darcy, K. M., Birrer, M. J. (2010) Translational research in the Gynecologic Oncology Group: evaluation of ovarian cancer markers, profiles, and novel therapies. Gynecol Oncol, 117(3), 429-439.
10. Vicent, M. J. and E. Perez-Paya, (2006) Poly-L-glutamic acid (PGA) aided inhibitors of apoptotic protease activating factor 1 (Apaf-1): an antiapoptotic polymeric nanomedicine. J Med Chem. 49(13): p. 3763-5.
11. Shaffer, S A., Baker-Lee C., Kenndy J. Lai M S, de Vries P, Buhler K, Singer J W, (2007) In vitro and in vivo metabolism of paditaxel poliglumex: identification of metabolites and active proteases. Cancer Chemother Pharmacol., 59(4): p. 537-48. Epub 2006 Aug. 19.
12. Leuchs, H. Br. (1906) Fiber die Glycin-carbonsaurenDtsch. Chem. Ges 39: 857.
13. Leuchs; H; Manasse, W. (1907) Ber Dtsch. Chem. Ges. 40: 3235.
14. Leuchs, H.; Geiger, W. (1908) Bar. Dtsch. Chem. Ges. 41: 1721.
15. Deming, T. (2000) Living polymerization of α-amino acid-N-carboxyanhydrides J. Polym. Sci., Part A: Polym. Chem. 38: 3011.
16. Kricheldorf, H. R. (2006) Polypeptides and 100 Years of Chemistry of a-Amino Acid N-Carboxyanhydrides Angew. Chem. Int. Ed. 45:5752-5784
17. Hadjichristidis, N.; Iatrou, H.; Pitsikalis, M.; Sakellariou, G. (2009) Synthesis of Well-Defined Polypeptide-Based Materials via the Ring-Opening Polymerization of r-Amino Acid N-Carboxyanhydrides Chem. Rev. 109: 5528-5578
18. Aliferis, T.; Iatrou, H.; Hadjichristidis, N. (2004) Living PolypeptidesBiomacromolecules 5: 1653-1656.

19. Aliferis, T.; Iatrou, H.; Hadjichristidis, N. (2005) Well-defined linear multiblock and branched polypeptides by linking chemistry. J. Polym. Sci., Part A 43; 4670.
20. Karatzas, A.; Iatrou, H.; Hadjichristidis, N.; Inoue, K.; Sugiyama, K.; Hirao, A. (2008) Complex Macromolecular Chimeras Biomacromolecules 9; 2072.
21. Dimitrov, I.; Schlaad, H. (2003) Synthesis of nearly monodisperse polystyrene-polypeptide block copolymers via polymerisation of N-carboxyanhydrides Chem. Commun. 2944.
22. Deming, T. (1997) Facile synthesis of block copolypeptides of defined architecture Nature 390: 386.
23. Deming, T.; Curtin, S. (2000) Chain Initiation Efficiency in Cobalt- and Nickel-Mediated Polypeptide Synthesis J. Am. Chem. Soc. 122; 5710.
24. Deming, T. (2006) Polypeptide Hybrid Copolymer Synthesis via NCA Polymerization, Adv. Polym. Sci., 202: 1-8.
25. Lu, H.; Cheng, J. (2007) Hexamethyldisilazane-Mediated Controlled Polymerization of α-Amino Acid N-Carboxyanhydrides J. Am. Chem. Soc. 129: 14114.
26. Lu, H.; Cheng, J. (2008)N-Trimethylsilyl Amines for Controlled Ring-Opening Polymerization of Amino Acid N-Carboxyanhydrides and Facile End Group Functionalization of Polypeptides J. Am. Chem. Soc. 130: 12562.
27. Vayaboury, W.; Giani, O.; Cottet, H.; Deratani, A.; Schue', F. (2004) Living Polymerization of α-Amino Acid N-Carboxyanhydrides (NCA) upon Decreasing the Reaction Temperature Macromol. Rapid Commun. 25: 1221.
28. Habraken G J M, Peeters M., Dietz, C H J T, Koning C E, Heise A. (2010). How controlled and versatile is N-carboxy anhydride (NCA) polymerization at 0_C? Effect of temperature on homo-, block- and graft (co) polymerization. 1, 514
29. Habraken G J M, Wilsens K H T M, Koning C E, Heise A (2011) Polym. Chem. Optimization of N-carboxyanhydride (NCA) polymerization by variation of reaction temperature and pressure. 2, 1322-1330
30. N. Hadjichristidis, H. Iatroua, M. Pitsikalisa, J. Mays Prog. Polym. Sd. 31 (2006) 1068-1132
31. Knobler, S. Bittner and M. Frankel, J. Chem. Soc., 1964, 3941-3951,
32. Knobler, S. Bittner, D. Virov and M. Frankel, *J. Chem. Soc.,* 1969, 1821-1824.

The invention claimed is:

1. A process for obtaining polyglutamates by means of controlled polymerization of N-carboxyanhydrides (NCAs) of alpha-amino acids using a nucleophilic salt of tetrafluoroborato as an initiator according to the reaction:

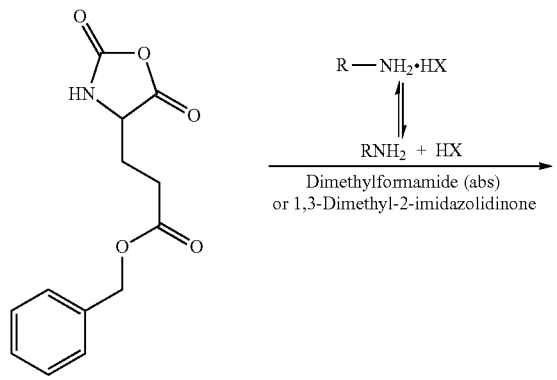
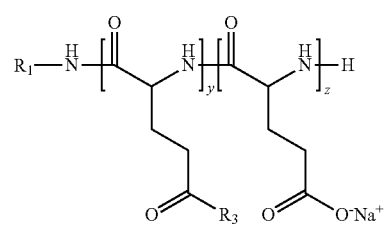

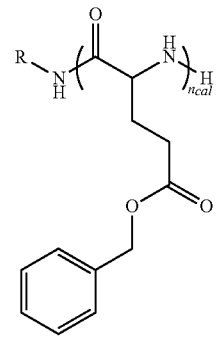

wherein:

R represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol (EG), or polyethylene glycol having a molecular weight of from 100 to 20,000 g/mol; $n_{cal}$ represents a whole number of units of γ-benzylglutamate in the polymer, ranging from 1 to 1,000; and X represents $BF_4$.

2. The process according to claim 1, wherein R is n-butyl.

3. The process according to claim 1, wherein R is polyethylene glycol having a molecular weight of from 100 to 20,000.

4. The process according to claim 1, wherein the final product obtained is in a di-block form having the formula:

wherein:

$R_1$ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;

$R_3$ represents an alkyl group, a C-terminal attachment group selected from an alkyne, an azide, a thiol, an halide, an activated thiol, an alkene, an activated ester, an activated alcohol, a protected amine, a maleimide group, an acetal and an activated carboxylic acid, ethylene glycol, polyethylene glycol from n=2 to n=16—wherein n is a number of repeating ethylene glycol units, an amino acid or a secondary or tertiary amino group;

y represents a whole number of glutamic units modified with $R_3$ group in the polymer, ranging from 1 to 1,000; and z represents a whole number of glutamic units without modification in the polymer, ranging from 1 to 1,000.

5. The process according to claim 1, wherein the final product obtained is in a tri-block form having the formula:

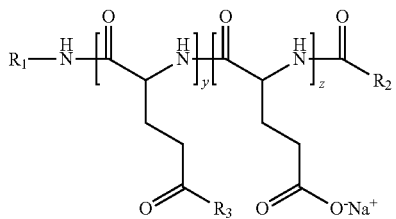

wherein:
- $R_1$ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;
- $R_2$ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol (PEG) having a molecular weight of from 100 to 20,000 g/mol, PEG-thiol or PEG-4-thiopyridyl;
- $R_3$ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16—wherein n is the number of repeating ethylene glycol units, an amino acid or a secondary or tertiary amino group;
- y represents a whole number of glutamic units modified with $R_3$ group in the polymer, ranging from 1 to 500;
- z represents a whole number of glutamic units not modified in the polymer, ranging from 1 to 1,000.

6. The process according to claim 5, through the reaction between a di-block form of polyethylene glycol-polyglutamic acid (PEG-PGA) and a derivative of functionalized PEG with an activated carboxyl group, obtaining tri-block systems having the formula:

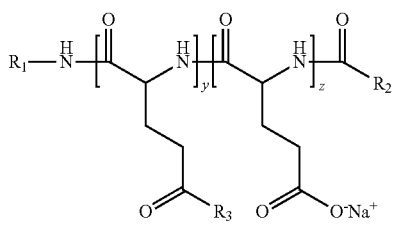

wherein
- $R_1$ represents a polyethylene glycol having a molecular weight of from 100 to 20,000 g/mol;
- $R_2$ represents a polyethylene glycol (PEG) having a molecular weight of from 100 to 20,000 g/mol, PEG-thiol or PEG-4-thiopyridyl;
- $R_3$ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16, an amino acid or a secondary or tertiary amino group;
- y represents a whole number of glutamic units modified with the $R_3$ group in the polymer, ranging from 1 to 500;
- z represents a whole number of glutamic units without modification in the polymer, ranging from 1 to 1,000.

7. The process according to claim 4, wherein $R_3$ is an amino acid selected from the group consisting of lysine, arginine, histidine and cysteine.

8. The process according to claim 5, wherein $R_3$ is an amino acid selected from the group consisting of lysine, arginine, histidine and cysteine.

9. The process according to claim 6, wherein $R_3$ is an amino acid selected from the group consisting of lysine, arginine, histidine and cysteine.

10. A polyglutamate obtained by the reaction between a di-block form of polyethylene glycol-polyglutamic acid (PEG-PGA) and a derivative functionalized PEG with an activated carboxyl group, obtaining tri-block systems having the formula:

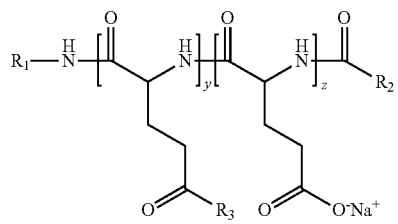

wherein:
- $R_1$ represents a polyethylene glycol having a molecular weight of from 100 to 20,000 g/mol;
- $R_2$ represents a polyethylene glycol (PEG) having a molecular weight of from 100 to 20,000 g/mol, PEG-thiol or PEG-4-thiopyridyl;
- $R_3$ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16, wherein n is the number of repeating ethylene glycol units, an amino acid or a secondary or tertiary amino group;
- y represents a whole number of glutamic units modified with the $R_3$ group in the polymer, ranging from 1 to 500;
- z represents a whole number of glutamic units without modification in the polymer, ranging from 1 to 1,000.

11. A polyglutamate obtained in a di-block form having the formula:

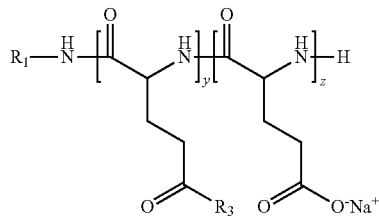

R₁ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;

R₃ represents an alkyl group, a C-terminal attachment group selected from an alkyne, an azide, a thiol, an halide, an activated thiol, an alkene, an activated ester, an activated alcohol, a protected amine, a maleimide group, an acetal and an activated carboxylic acid, ethylene glycol, polyethylene glycol from n=2 to n=16—wherein n is the number of repeating ethylene glycol units, an amino acid or a secondary or tertiary amino group;

y represents a whole number of glutamic units modified with R₃ group in the polymer, ranging from 1 to 1,000; and z represents a whole number of glutamic units without modification in the polymer, ranging from 1 to 1,000.

12. The polyglutamate according to claim 11, wherein the amino acid of R₃ is selected from lysine, arginine, histidine and cysteine.

13. A conjugate comprising low molecular weight drugs, peptides, proteins, antibodies, near infrared fluorescent probes, coordination complexes for MRI or PET or SPECT probes, and the polyglutamate as defined in claim 11, wherein the bioactive agents, the near infrared fluorescent probes, the coordination complexes for MRI, and the PET or SPECT probes are conjugated through R₂ and/or R₃.

14. Drug delivery compound comprising the polyglutamate of claim 11.

15. Molecular imaging diagnostic agent comprising the polyglutamate of claim 11.

16. A polyglutamate obtained in a tri-block form having the formula:

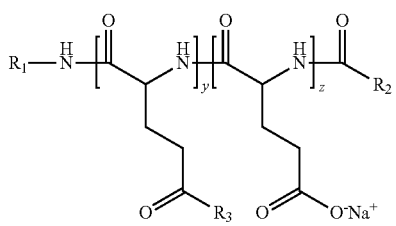

wherein:

R₁ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;

R₂ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol (PEG) having a molecular weight of from 100 to 20,000 g/mol, PEG-thiol or PEG-4-thiopyridyl;

R₃ represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16—wherein n is the number of repeating ethylene glycol units, an amino acid or a secondary or tertiary amino group;

y represents a whole number of glutamic units modified with R₃ group in the polymer, ranging from 1 to 500;

z represents a whole number of glutamic units not modified in the polymer, ranging from 1 to 1,000.

17. The polyglutamate according to claim 16, wherein the amino acid of R₃ is selected from lysine, arginine, histidine and cysteine.

18. A conjugate comprising low molecular weight drugs, peptides, proteins, antibodies, near infrared fluorescent probes, coordination complex for MRI or PET or SPECT probes, and the polyglutamate as defined in claim 16, wherein the bioactive agents, the near infrared fluorescent probes, the coordination complexes for MRI, and the PET or SPECT probes are conjugated through R₂ and/or R₃.

19. Drug delivery compound comprising the polyglutamate of claim 16.

20. Molecular imaging diagnostic agent comprising the polyglutamate of claim 16.

21. The polyglutamate according to claim 10, wherein the amino acid of R₃ is selected from lysine, arginine, histidine and cysteine.

22. Drug delivery compound comprising the polyglutamate of claim 10.

23. Molecular imaging diagnostic agent comprising the polyglutamate of claim 10.

* * * * *

UNITED STATES PATENT AND TRADEMARK OFFICE
CERTIFICATE OF CORRECTION

PATENT NO. : 9,623,125 B2
APPLICATION NO. : 14/351904
DATED : April 18, 2017
INVENTOR(S) : Maria Jesus Vicent Docon et al.

It is certified that error appears in the above-identified patent and that said Letters Patent is hereby corrected as shown below:

In the Specification

Column 1, Line 7: "O-Amino" should be --α-Amino--
Column 1, Line 52: "several gram scale" should be --several grams scale--
Column 2, Line 13: "[25-26]" should be --[25-26].--
Column 3, Line 58: "(NCA)" should be --(NCA).--
Column 3, Line 61: "DMF" should be --DMF.--
Column 3, Line 62: "GPC should be --GPC.--
Column 3, Line 64: "molecular" should be --molecular.--
Column 3, Line 67: "NMR," should be --NMR.--
Column 4, Line 2: "propagylamine" should be --propagylamine.--
Column 4, Line 47: "TB-OG200[P: 43" should be --TB-OG200 [P: 43--
Column 4, Line 57: "TB-OG200[P: 43" should be --TB-OG200 [P: 43--
Column 4, Line 66: "like endocytosis).G2000," should be --like endocytosis). G2000,--
Column 5, Line 15: "acetonitrile(AcN)" should be --acetonitrile (AcN).--
Column 5, Line 27: "Ventral position" should be --Ventral position.--
Column 5, Line 30: "TB800-DTPA/Gd" should be --TB800-DTPA/Gd.--
Column 5, Line 32: "TB800-DTPA/Gd" should be --TB800-DTPA/Gd.--
Column 5, Line 38: "and dorsal sections" should be --and dorsal sections.--
Column 6, before Line 23, please insert the following:
--In another embodiment, the invention relates to the process as defined above, wherein R is n-butyl.
In another embodiment, the invention relates to the process as defined above, wherein R is polyethylene glycol having a molecular weight of from 100 to 20,000 g/mol.
In another embodiment, the invention relates to the process as defined above, wherein the final product obtained is in a di-block form having the formula:

Signed and Sealed this
Thirtieth Day of October, 2018

Andrei Iancu
*Director of the United States Patent and Trademark Office*

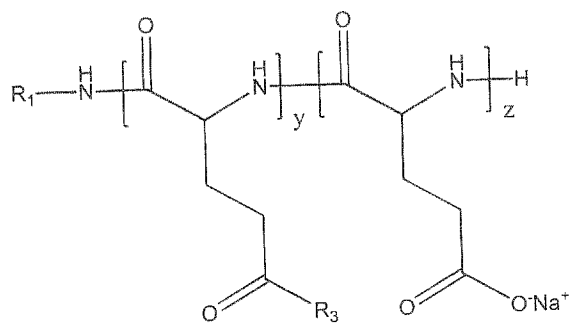

wherein:
R1 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;
R3 represents an alkyl group, a C-terminal attachment group selected from an alkyne, an azide, a thiol, an halide, an activated thiol, an alkene, an activated ester, an activated alcohol, a protected amine, a maleimide group, an acetal and an activated carboxylic acid, ethylene glycol, polyethylene glycol from n=2 to n=16, wherein n is the number of repeating ethylene glycol units, an amino acid or a secondary or tertiary amino group;
y represents a whole number of glutamic units modified with R3 group in the polymer, ranging from 1 to 1,000; and
z represents a whole number of glutamic units without modification in the polymer, ranging from 1 to 1,000.
In another embodiment, the invention relates to the process as defined above, wherein the final product obtained is in a tri-block form having the formula:

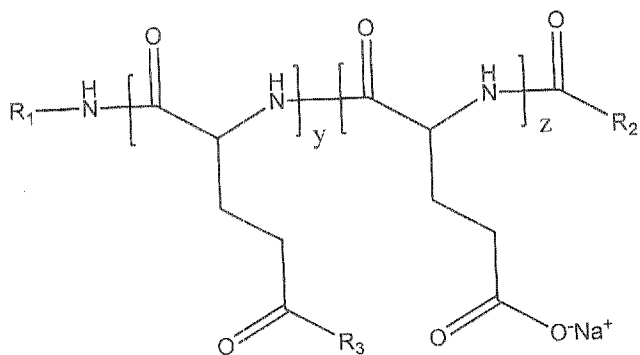

wherein:
R1 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;
R2 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol (PEG) having a molecular weight of from 100 to 20,000 g/mol, PEG-thiol or PEG-4-thiopyridyl;
R3 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16, wherein n is the number of repeating ethylene glycol units, an amino acid or a secondary or tertiary amino group;

y represents a whole number of glutamic units modified with R3 group in the polymer, ranging from 1 to 500;

z represents a whole number of glutamic units not modified in the polymer, ranging from 1 to 1,000.

In another embodiment, the invention relates to the process as defined above, through the reaction between a di-block form of polyethylene glycol-polyglutamic acid (PEG-PGA) and a derivative of functionalized PEG with an activated carboxyl group, obtaining tri-block systems having the formula:

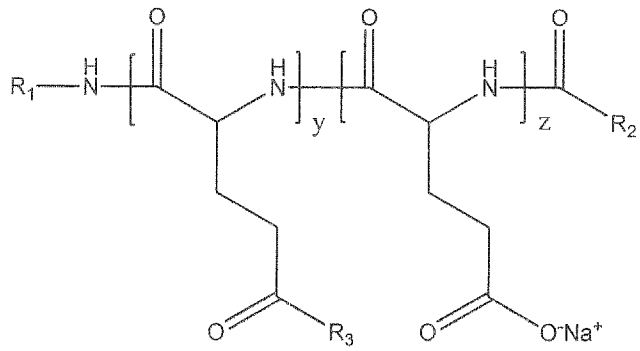

wherein:

R1 represents a polyethylene glycol having a molecular weight of from 100 to 20,000 g/mol;

R2 represents a polyethylene glycol (PEG) having a molecular weight of from 100 to 20,000 g/mol, PEG-thiol or PEG-4-thiopyridyl;

R3 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16, an amino acid or a secondary or tertiary amino group;

y represents a whole number of glutamic units modified with the R3 group in the polymer, ranging from 1 to 500;

z represents a whole number of glutamic units without modification in the polymer, ranging from 1 to 1,000.

In another embodiment, the invention relates to any of the processes as defined above, wherein R3 is an amino acid selected from the group consisting of lysine, arginine, histidine and cysteine.

Another aspect of the present invention relates to a polyglutamate obtained by the reaction between a di-block form of polyethylene glycol-polyglutamic acid (PEG-PGA) and a derivative functionalized PEG with an activated carboxyl group, obtaining tri-block systems having the formula:

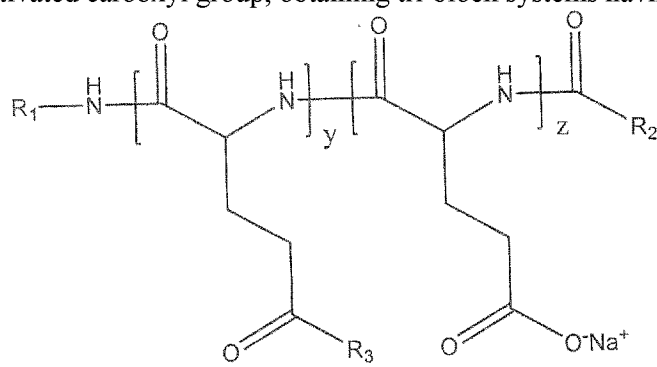

wherein:
R1 represents a polyethylene glycol having a molecular weight of from 100 to 20,000 g/mol;
R2 represents a polyethylene glycol (PEG) having a molecular weight of from 100 to 20,000 g/mol, PEG-thiol or PEG-4-thiopyridyl;
R3 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16, wherein n is the number of repeating ethylene glycol units, an amino acid or a secondary or tertiary amino group;
y represents a whole number of glutamic units modified with the R3 group in the polymer, ranging from 1 to 500;
z represents a whole number of glutamic units without modification in the polymer, ranging from 1 to 1,000.
Another aspect of the present invention relates to a polyglutamate obtained in a di-block form having the formula:

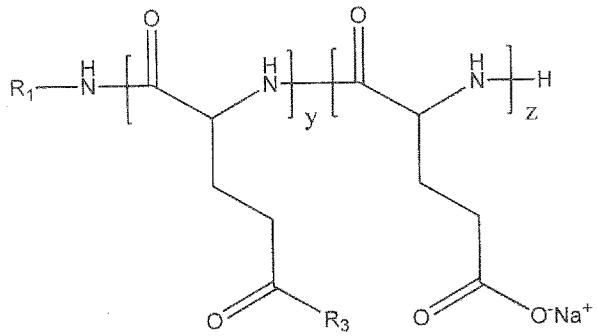

R1 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;
R3 represents an alkyl group, a C-terminal attachment group selected from an alkyne, an azide, a thiol, an halide, an activated thiol, an alkene, an activated ester, an activated alcohol, a protected amine, a maleimide group, an acetal and an activated carboxylic acid, ethylene glycol, polyethylene glycol from n=2 to n=16,
wherein n is the number of repeating ethylene glycol units, an amino acid or a secondary or tertiary amino group;
y represents a whole number of glutamic units modified with R3 group in the polymer, ranging from 1 to 1,000; and
z represents a whole number of glutamic units without modification in the polymer, ranging from 1 to 1,000.
In another embodiment, the invention relates to the polyglutamate as defined above wherein the amino acid of R3 selected from lysine, arginine, histidine and cysteine.
In another embodiment, the invention relates to a drug delivery compound comprising the polyglutamate as defined above.
In another embodiment, the invention relates to a molecular imaging diagnostic agent comprising the polyglutamate of claim as defined above.

In another embodiment, the invention relates to the polyglutamate as defined above, wherein the amino acid of of R3 is selected from lysine, arginine, histidine and cysteine.

Another aspect of the present invention relates to a conjugate comprising low molecular weight drugs, peptides, proteins, antibodies, near infrared fluorescent probes, coordination complexes for MRI or PET or SPECT probes, and the polyglutamate as defined above, wherein the bioactive agents, the near infrared fluorescent probes, the coordination complexes for MRI, and the PET or SPECT probes are conjugated through R2 and/or R3.

Another aspect of the present invention relates to a drug delivery compound comprising the polyglutamate as defined above.

Another aspect of the present invention relates to a molecular imaging diagnostic agent comprising the polyglutamate as defined above.

Another aspect of the present invention relates to a polyglutamate obtained in a tri-block form having the formula:

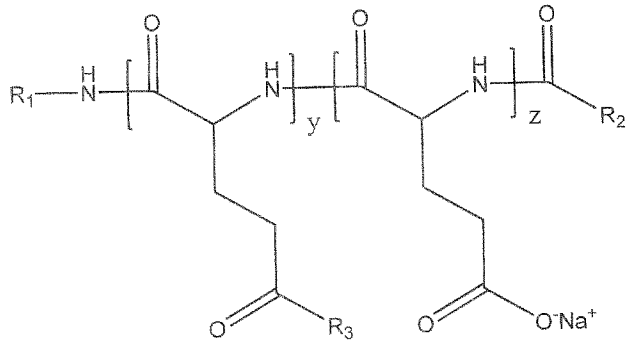

wherein:

R1 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, or polyethylene glycol having a molecular weight of from 100 to 20,000 g/mol;

R2 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol (PEG) having a molecular weight of from 100 to 20,000 g/mol, PEG-thiol or PEG-4-thiopyridyl;

R3 represents an alkyl group, a C-terminal attachment group selected from an alkyne, an azide, a thiol, a halide, an activated thiol, an alkene, an activated ester, an activated alcohol, a protected amine, a maleimide group, an acetal, and an activated carboxylic acid, ethylene glycol, polyethylene glycol from n=2 to n=16, wherein n is the number of repeating ethylene glycol units, an amino acid or a secondary or tertiary amino group;

y represents a whole number of glutamic units modified with R3 group in the polymer, ranging from 1 to 500;

z represents a whole number of glutamic units not modified in the polymer, ranging from 1 to 1,000.

In another embodiment, the invention relates to the polyglutamate as defined above, wherein the amino acid of R3 is selected from lysine, arginine, histidine and cysteine.

Another aspect of the present invention relates to a conjugate comprising low molecular weight drugs, peptides, proteins, antibodies, near infrared fluorescent probes, coordination complex for MRI or PET or SPECT probes, and the polyglutamate as defined above, wherein the bioactive agents, the near

CERTIFICATE OF CORRECTION (continued)

infrared fluorescent probes, the coordination complexes for MRI, and the PET or SPECT probes are conjugated through R2 and/or R3.

Another aspect of the present invention relates to a drug delivery compound comprising the polyglutamate as defined above.

Another aspect of the present invention relates to a molecular imaging diagnostic agent comprising the polyglutamate as defined above.--

Column 6, Line 27 to Column 7, Line 24: please delete this section

Column 7, Line 35: "represents n-Butylamine" should be --represents n-butylamine--

Column 11, Line 25: "was dissolve in 3 mL" should be --was dissolved in 3 mL--

Column 12, Line 9: "metoxypolyethylenglicolammonium" should be --metoxypolyethylene glycol ammonium--

Column 12, Line 29: "(polyethylenglycol)" should be --(polyethylene glycol)--

Column 16, Line 34: "n represents number of y-benzyl-glutamate units in the polymer, from 1 to 1000" should be --ncal represents number of y-benzyl-glutamate units in the polymer, from 1 to 1000.--

Column 18, Line 50: "Defined C-terminal" should be --defined C-terminal--

Column 18, Line 55: "number of ethylenglycol" should be --number of ethylene glycol--

Column 18, Line 60: "number of ethylenglycol" should be --number of ethylene glycol--

Column 20, Line 51: "ratio monomer:PEG," should be --ratio monomer: PEG,--

Column 21, Line 21: "Defined C-terminal" should be --defined C-terminal--

Column 21, Line 26: "number of ethylenglycol" should be --number of ethylene glycol--

Column 21, Line 31: "number of ethylenglycol" should be --number of ethylene glycol--

Column 23, Line 36: "Defined C-terminal" should be --defined C-terminal--

Column 23, Line 43: "form 1 to 1000" should be --from 1 to 1000--

Column 23, Line 56: "50 samples" should be --Fifty samples--

Column 24, Line 54 to Column 25, Line 33: please replace the formula with the following:

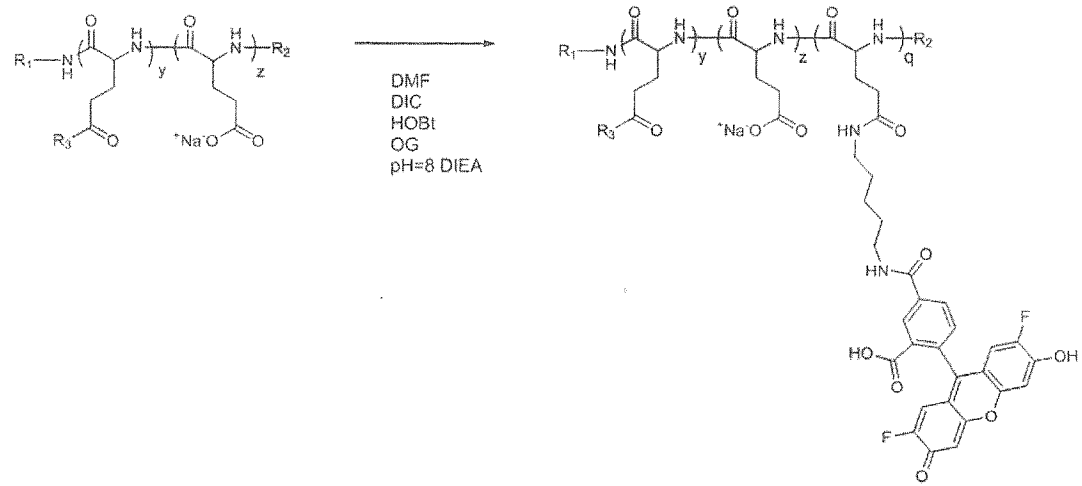

Column 25, Line 36: "Defined C-terminal" should be --defined C-terminal--

Column 25, Line 40: "ethylenglicol" should be --ethylene glycol--

Column 25, Line 41: "polyethylenglicol" should be --polyethylene glycol--

Column 25, Line 43: "Defined C-terminal" should be --defined C-terminal--

Column 25, Line 47: "ethylenglicol" should be --ethylene glycol--

Column 25, Line 48: "polyethylenglicol" should be --polyethylene glycol--

Column 25, Line 50: "Defined C-terminal" should be --defined C-terminal--

Column 25, Line 54: "ethylenglicol" should be --ethylene glycol--
Column 25, Line 55: "polyethylenglicol" should be --polyethylene glycol--
Column 25, Lines 56-57: "arginine, imidazole, histidine" should be --arginine, histidine--
Column 25, Lines 59-60: Please delete the line "x represents number of monomer units into definition R1, from 1 to 500"
Column 25, Lines 65-66: Please delete the line "p represents number of monomer units included into R3 definition, from 1 to 500"
Column 26, Lines 4-5: "N,N'Diisopropylcarbodiimide" should be --N,N' Diisopropylcarbodiimide--
Column 27, Lines 3-40: Please replace the formula with the following:

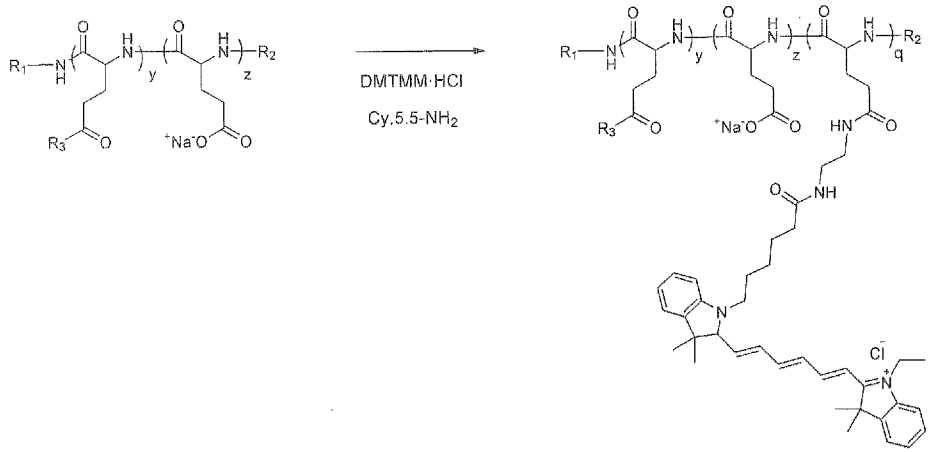

Column 27, Line 42: "Defined C-terminal" should be --defined C-terminal--
Column 27, Line 46: "ethylenglicol" should be --ethylene glycol--
Column 27, Line 47: "polyethylenglicol" should be --polyethylene glycol--
Column 27, Line 50: "Defined C-terminal" should be --defined C-terminal--
Column 27, Line 54: "ethylenglicol" should be --ethylene glycol--
Column 27, Line 55: "polyethylenglicol" should be --polyethylene glycol--
Column 27, Line 57: "Defined C-terminal" should be --defined C-terminal--
Column 27, Line 62: "polyethylenglicol" should be --polyethylene glycol--
Column 27, Lines 63-64: "arginine, imidazole, histidine" should be --arginine, histidine--
Column 27, Lines 66-67: Please delete the line "x represents number of monomer units into definition R1, from 1 to 500"
Column 28, Lines 5-6: Please delete the line "p represents number of monomer units included into R3 definition, from 1 to 500"
Column 28, Line 18: "300 L" should be --300 μL--
Column 30, Lines 4-5: Please delete the line "x represents number of units of glutamic modified with propargylamine, from 1 to 1000"
Column 32, Lines 29-30: Please delete the line "x represents number of units of glutamic modified with ethilenglycol, from 1 to 1000"
Column 32, Lines 35-36: "oligoethylenglicol" should be --oligoethylene glycol--
Column 32, Line 37: "oligoethylengNcol" should be --oligoethylene glycol--
Column 32, Line 38: "ethylenglicol" should be --ethylene glycol--
Column 32, Line 47: "oligoethylenglicol" should be --oligoethylene glycol--
Column 32, Line 51: "ethylenglicol" should be --ethylene glycol--
Column 33, Line 44: "oligoethylengNcol" should be --oligoethylene glycol--

CERTIFICATE OF CORRECTION (continued)
U.S. Pat. No. 9,623,125 B2

Column 33, Lines 52-53: "metoxy-oligoethylenglycol-amine" should be --metoxy-oligoethylene glycol-amine--
Column 34, Lines 66-67: "ethylenglicol" should be --ethylene glycol--
Column 36, Lines 66-67: "ethylenglycol" should be --ethylene glycol--
Column 40, Line 50-Column 41, Line 26: Please replace the formula with the following:

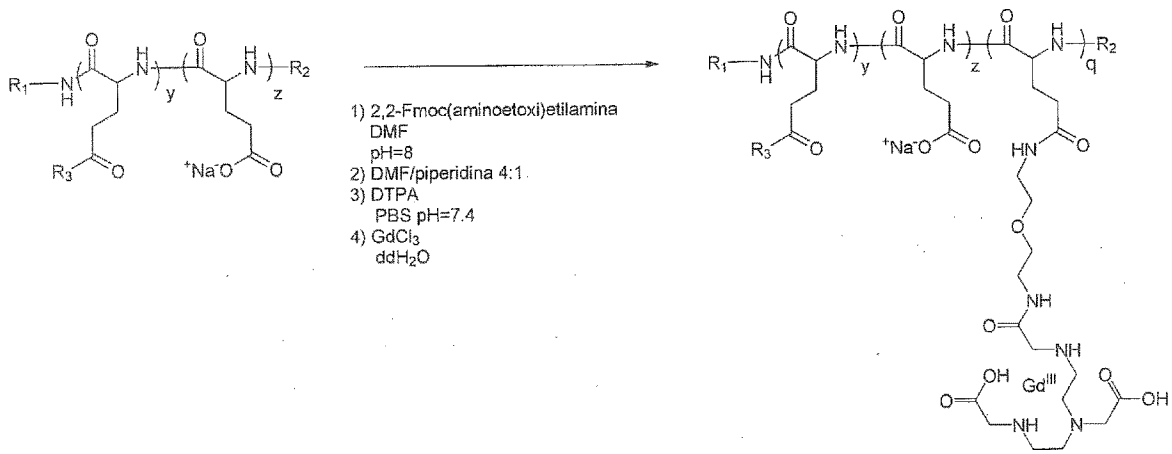

Column 41, Line 29: "Defined C-terminal" should be --defined C-terminal--
Column 41, Line 33: "ethylenglicol" should be --ethylene glycol--
Column 41, Line 34: "polyethylenglicol" should be --polyethylene glycol--
Column 41, Line 36: "Defined C-terminal" should be --defined C-terminal--
Column 41, Line 41: "ethylenglicol" should be --ethylene glycol--
Column 41, Line 42: "polyethylenglicol" should be --polyethylene glycol--
Column 41, Line 45: "Defined C-terminal" should be --defined C-terminal--
Column 41, Line 49: "ethylenglicol" should be --ethylene glycol--
Column 41, Line 50: "polyethylenglicol" should be --polyethylene glycol--
Column 41, Lines 51-52: "arginine, imidazole, histidine" should be --arginine, histidine--
Column 41, Lines 54-55: Please delete the line "x represents number of monomer units into definition R1, from 1 to 500"
Column 41, Lines 61-62: Please delete the line "p represents number of monomer units included into R3 definition, from 1 to 500"
Column 42, Line 48-Column 43, Line 21: Please replace the formula with the following:

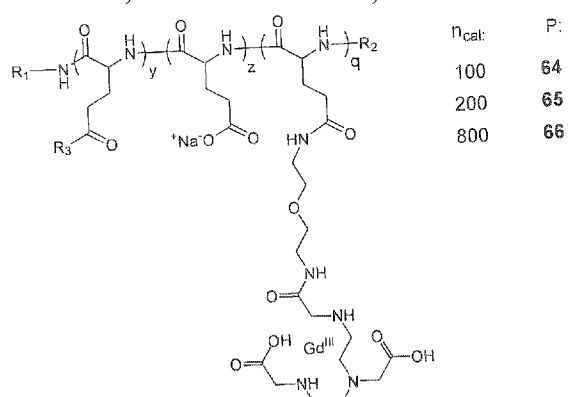

| $n_{cal}$: | P: |
|---|---|
| 100 | 64 |
| 200 | 65 |
| 800 | 66 |

Column 43, Lines 23-24: Please delete the line "x represents number of monomer unit included into R 1 definition, from 1 to 500"

Column 43, Line 50-Column 44, Line 21: Please replace the formula with the following:

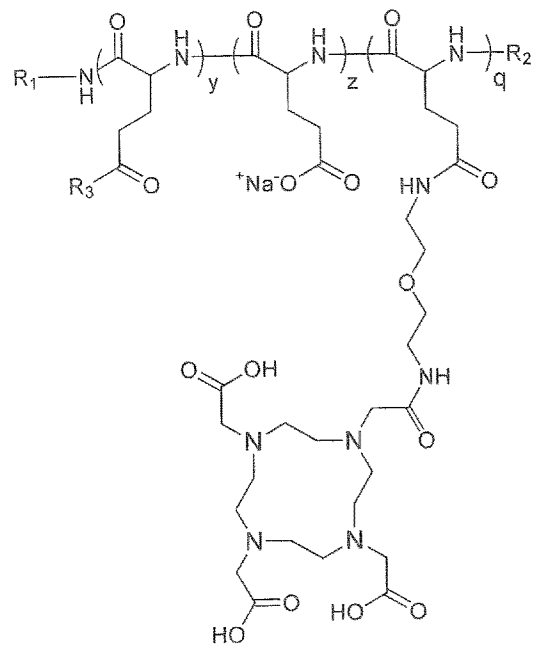

Column 44, Line 24: "Defined C-terminal" should be --defined C-terminal--
Column 44, Line 28: "ethylenglicol" should be --ethylene glycol--
Column 44, Line 29: "polyethylenglicol" should be --polyethylene glycol--
Column 44, Line 31: "Defined C-terminal" should be --defined C-terminal--
Column 44, Line 35: "ethylenglicol" should be --ethylene glycol--
Column 44, Line 36: "polyethylenglicol" should be --polyethylene glycol--
Column 44, Line 38: "Defined C-terminal" should be --defined C-terminal--
Column 44, Line 42: "ethylenglicol" should be --ethylene glycol--
Column 44, Line 43: "polyethylenglicol" should be --polyethylene glycol--
Column 44, Lines 44-45: "arginine, imidazole, histidine" should be --arginine, histidine--
Column 44, Lines 47-48: Please delete the line "x represents number of monomer units into definition R1, from 1 to 500"
Column 45, Line 59: "(FIG. 2A)" should be --(FIG. 10A)--
Column 45, Line 60: "(FIG. 2Ab)" should be --(FIG. 10B)--
Column 46, Line 38: "100 L" should be --100 µL--
Column 46, Line 45: "100 L" should be --100 µL--
Column 46, Line 53: "100 L" should be --100 µL--